(12) United States Patent
Ricci

(10) Patent No.: US 11,948,685 B2
(45) Date of Patent: Apr. 2, 2024

(54) SYSTEMS AND METHODS FOR GENERATING A DENTAL RECOMMENDATION BASED ON IMAGE PROCESSING

(71) Applicant: Richard Ricci, New York, NY (US)

(72) Inventor: Richard Ricci, New York, NY (US)

(*) Notice: Subject to any disclaimer, the term of this patent is extended or adjusted under 35 U.S.C. 154(b) by 504 days.

(21) Appl. No.: 17/138,641

(22) Filed: Dec. 30, 2020

(65) Prior Publication Data

US 2021/0201489 A1 Jul. 1, 2021

Related U.S. Application Data

(60) Provisional application No. 62/955,321, filed on Dec. 30, 2019.

(51) Int. Cl.
| | | |
|---|---|---|
| *G16H 50/20* | (2018.01) | |
| *G06F 18/21* | (2023.01) | |
| *G06Q 30/0601* | (2023.01) | |
| *G06T 7/00* | (2017.01) | |
| *G06T 7/11* | (2017.01) | |
| *G16H 10/60* | (2018.01) | |
| *G16H 30/20* | (2018.01) | |

(Continued)

(52) U.S. Cl.
CPC ......... *G16H 50/20* (2018.01); *G06F 18/2178* (2023.01); *G06Q 30/0631* (2013.01); *G06T 7/0012* (2013.01); *G06T 7/0014* (2013.01); *G06T 7/11* (2017.01); *G16H 10/60* (2018.01); *G16H 30/20* (2018.01); *G16H 40/20* (2018.01); *G16H 40/67* (2018.01); *G16H 70/20* (2018.01); *G16H 70/60* (2018.01); *G16H 80/00* (2018.01); *G06T 2207/10* (2013.01); *G06T 2207/20081* (2013.01); *G06T 2207/20084* (2013.01); *G06T 2207/20101* (2013.01); *G06T 2207/30036* (2013.01)

(58) Field of Classification Search
CPC ........ G16H 50/20; G16H 10/60; G16H 30/20; G16H 40/20; G16H 40/67; G16H 70/20; G16H 70/60; G16H 80/00; G16H 30/40; G06F 18/2178; G06Q 30/0631; G06Q 30/0282; G06Q 50/22; G06T 7/0012; G06T 7/0014; G06T 7/11; G06T 2207/10; G06T 2207/20081; G06T 2207/20084; G06T 2207/20101; G06T 2207/30036
USPC ....................................................... 382/128
See application file for complete search history.

(56) References Cited

U.S. PATENT DOCUMENTS

| | | | | |
|---|---|---|---|---|
| 2011/0050848 A1* | 3/2011 | Rohaly | .................. | G06T 15/10 348/43 |
| 2019/0313963 A1* | 10/2019 | Hillen | .................. | G06V 10/764 |

* cited by examiner

*Primary Examiner* — Charlotte M Baker

(57) ABSTRACT

Disclosed here is a method of generating a dental recommendation based on image processing. Further, the method may include receiving at least one patient data comprising at least one image from at least one patient device. Further, the method may include retrieving at least one dental dataset. Further, the method may include analyzing the at least one patient data and the at least one dental dataset. Further, the method may include generating at least one landmark based on the analyzing. Further, the method may include retrieving at least one dental reference dataset. Further, the method may include processing the at least one landmark and the at least one dental reference dataset, determining at least one dental recommendation based on the processing, transmitting the at least one dental recommendation to at least one external device and storing the at least one dental recommendation.

20 Claims, 12 Drawing Sheets

(51) Int. Cl.
*G16H 40/20* (2018.01)
*G16H 40/67* (2018.01)
*G16H 70/20* (2018.01)
*G16H 70/60* (2018.01)
*G16H 80/00* (2018.01)

SYSTEMS AND METHODS FOR GENERATING A DENTAL RECOMMENDATION BASED ON IMAGE PROCESSING

FIELD OF THE INVENTION

Generally, the present invention relates to the field of data processing. More specifically, the present invention relates to systems and methods for generating a dental recommendation based on image processing.

BACKGROUND OF THE INVENTION

Existing techniques for generating a dental recommendation based on image processing are deficient with regard to several aspects. For instance, current technologies do not generate a dental recommendation (such as dental treatment aid, a dental product recommendation, etc.) based on an artificial intelligence model processing of a dental image. Furthermore, current technologies do not facilitate a transaction of the dental recommendation.

Therefore, there is a need for improved systems and methods for generating a dental recommendation based on image processing that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed here is a method of generating a dental recommendation based on image processing in accordance with some embodiments. Further, the method may include receiving, using a communication device, at least one patient data comprising at least one image from at least one patient device. Further, the method may include retrieving, using a storage device, at least one dental dataset. Further, the method may include analyzing, using a processing device, the at least one patient data and at least one dental dataset. Further, the at least one dental dataset is associated with the at least one patient data. Further, the at least one dental dataset comprises a classified dental image dataset. Further, the method may include generating, using the processing device, at least one landmark based on the analyzing. Further, the at least one landmark comprises at least one dental characteristic associated with the at least one patient data. Further, the method may include retrieving, using the storage device, at least one dental reference dataset. Further, the method may include processing, using the processing device, the at least one landmark and the at least one dental reference dataset. Further, the method may include determining, using the processing device, at least one dental recommendation based on the processing. Further, the method may include transmitting, using the communication device, the at least one dental recommendation to at least one external device. Further, the method may include storing, using the storage device, the at least one dental recommendation.

According to some embodiments, a system of generating a dental recommendation based on image processing is disclosed. Further, the system may include a communication device configured for receiving at least one patient data comprising at least one image from at least one patient device. Further, the communication device may be configured for transmitting at least one dental recommendation to at least one external device. Further, the system may include a processing device configured for analyzing the at least one patient data and at least one dental dataset. Further, the at least one dental dataset is associated with the at least one patient data. Further, the at least one dental dataset comprises a classified dental image dataset. Further, the processing device may be configured for generating at least one landmark based on the analyzing. Further, the at least one landmark comprises at least one dental characteristic associated with the at least one patient data. Further, the processing device may be configured for processing the at least one landmark and at least one dental reference dataset. Further, the processing device may be configured for determining the at least one dental recommendation based on the processing. Further, the system may include a storage device configured for retrieving the at least one dental dataset, retrieving the at least one dental reference dataset and storing the at least one dental recommendation.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this invention, illustrate various embodiments of the present invention. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present invention. This text is included for illustrative, non-limiting, explanatory purposes of certain embodiments detailed in the present invention.

DETAILED DESCRIPTION OF THE INVENTION

Figure 1:
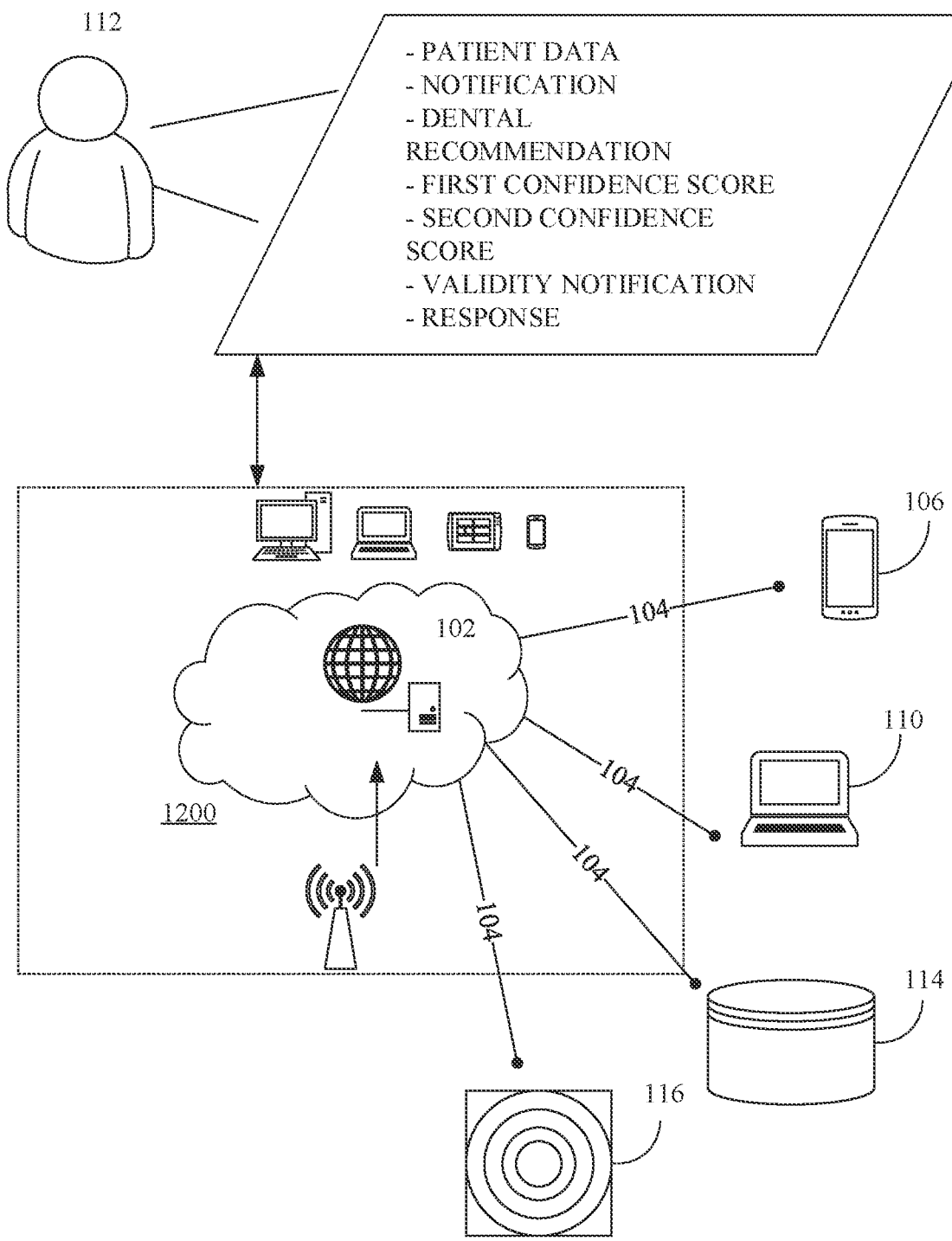
FIG. 1 is an illustration of an online platform consistent with various embodiments of the present invention.

As a preliminary matter, it will readily be understood by one having ordinary skill in the relevant art that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the embodiments of the present invention. Other embodiments also may be discussed for additional illustrative purposes in providing a full and enabling invention. Moreover, many embodiments, such as adaptations, variations, modifications, and equivalent arrangements, will be implicitly disclosed by the embodiments described herein and fall within the scope of the present invention.

Accordingly, while embodiments are described herein in detail in relation to one or more embodiments, it is to be understood that this invention is illustrative and exemplary of the present invention, and are made merely for the purposes of providing a full and enabling invention. The detailed invention herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the claims found herein and/or issuing here from The present invention contains headers. It should be understood that these headers are used as references and are not to be construed as limiting upon the subjected matter disclosed under the header.

The present invention includes many aspects and features. Moreover, while many aspects and features relate to, and are described in the context of methods and systems of generating a dental recommendation based on image processing, embodiments of the present invention are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, and at least one sensor. Examples of the one or more client devices and/or the server computer may include, a desktop computer, a laptop computer, a tablet, a personal digital assistant, a portable electronic device, a wearable computer, a smartphone, an Internet of Things (IoT) device, a smart electrical appliance, a video game console, a rack server, a supercomputer, a mainframe computer, mini-computer, microcomputer, a storage server, an application server (e.g. a mail server, a web server, a real-time communication server, an FTP server, a virtual server, a proxy server, a DNS server, etc.), and so on. Further, one or more client devices and/or the server computer may be configured for executing a software application such as, for example, but not limited to, an operating system (e.g. Windows, macOS, Unix, Linux, Android, etc.) in order to provide a user interface (e.g., GUI, touch-screen based interface, voice-based interface, gesturebased interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, a public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end-user, an admin, a service provider, a service consumer, an agent, a broker and a representative thereof. Further, the user as defined herein may refer to a human, an animal or an artificially intelligent being in any state of existence, unless stated otherwise, elsewhere in the present invention. Further, in some embodiments, the one or more users may be required to successfully perform authentication in order for the control input to be effective. In general, a user of the one or more users may perform authentication based on the possession of a secret human-readable secret data (e.g. username, password, passphrase, PIN, secret question, secret answer, etc.) and/or possession of a machine-readable secret data (e.g. encryption key, decryption key, bar codes, etc.) and/or possession of one or more embodied characteristics unique to the user (e.g., biometric variables such as but not limited to, fingerprint, palm-print, voice characteristics, behavioral characteristics, facial features, iris pattern, heart rate variability, evoked potentials, brain waves, and so on) and/or possession of a unique device (e.g., a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g., transmitting and/or receiving) with one or more sensor devices and/or one or more actuators in order to perform authentication. For example, the one or more steps may include receiving, using the communication device, the secret human-readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device, etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor, etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the one or more steps).

Further, the one or more steps of the method may be performed one or more number of times. Additionally, the one or more steps may be performed in any order other than as exemplarily disclosed herein, unless explicitly stated otherwise, elsewhere in the present invention. Further, two or more steps of the one or more steps may, in some embodiments, be simultaneously performed, at least in part. Further, in some embodiments, there may be one or more time gaps between the performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data there between corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present invention describes systems and methods for generating a dental recommendation based on image processing. Further, the field of embodiment relates to a system to provide artificial intelligence processing of a dental image for e-commerce. The dental image (received from a source such as an x-ray, a camera, or an image capturing device) may be processed by an artificial intelligence mechanism to produce a diagnostic treatment aid and/or a product recommendation aid for e-commerce.

Dental images processed with artificial intelligence for e-commerce is described. In an example scenario, an aggregator server receives a dental image. A dental image may be processed with one and/or multiple resolutions with a deep neural network to detect different dental image landmarks by matching and identifying the dental image to an annotated dental image anatomy dataset and/or an annotated dental image pathology dataset. An annotated dental image anatomy dataset and/or an annotated dental image pathology dataset may be processed with supervised learning and/or unsupervised learning to produce an identified dental image landmark. Further, an annotated dental image anatomy dataset and/or an annotated dental image pathology dataset may be annotated by at least one of a dental professional, a health care professional, an individual, e-commerce organization.

A dental image with an identified dental image landmark may be matched to a supervised and/or unsupervised dental image landmark dataset and/or a supervised and/or unsupervised annotated dental image landmark dataset. Further, the dental image may be matched directly to a supervised and/or unsupervised annotated dental image landmark dataset. A supervised and/or unsupervised annotated dental image landmark dataset may be obtained and/or annotated from at least one of a dental professional, a health care professional, an individual, e-commerce organization.

A dental professional, a health care professional, an individual and an e-commerce organization may also annotate a dental image with treatment options to produce a supervised and/or unsupervised annotated dental treatment dataset.

With multiple resolutions, each deep neural network may learn to detect different dental image landmarks of a dental image and to match and identify with a supervised and/or unsupervised dental image landmark dataset. The process may continue to match and identify the dental image landmark of a dental image to a supervised and/or unsupervised annotated dental treatment dataset.

The supervised and/or unsupervised annotated dental treatment dataset may match and identify dental image landmarks of a dental image and provide treatment recommendations and/or no treatment recommendations for at least one dental image landmark.

Further, the dental image may be matched directly to the supervised and/or unsupervised annotated dental treatment dataset.

A dental image, a supervised and/or unsupervised annotated dental image anatomy dataset and/or a supervised and/or unsupervised annotated dental image pathology dataset, a dental image landmark, a supervised and/or unsupervised dental image landmark dataset, a supervised and/or unsupervised annotated dental image landmark dataset and a supervised and/or unsupervised annotated dental treatment dataset may be merged and correlated to an annotated dental treatment dataset for further processing.

The supervised and/or unsupervised annotated dental image landmark dataset and/or the supervised and/or unsupervised annotated dental treatment dataset are configured to continually merge and correlate additional annotated dental images from at least one of a dental professional, a health care professional, an individual, e-commerce organization. Further, additional annotated dental images may be obtained and/or processed with at least one of: supervised learning, unsupervised learning, rewards training, transfer learning, confidence values, confidence scores, reactive memory, non-reactive memory, a memory of dataset, a system of artificial intelligence with memory.

A supervised and/or unsupervised annotated dental image anatomy dataset, a supervised and/or unsupervised annotated dental image pathology dataset, a supervised and/or unsupervised
    dental image landmark dataset, a supervised and/or unsupervised annotated dental image landmark dataset, a supervised and/or unsupervised annotated dental treatment dataset and an annotated dental treatment dataset are configured to identify and correct for missing image information.

Further, the supervised and/or unsupervised annotated dental image landmark dataset is configured to deep learn dental image landmarks and the supervised and/or unsupervised annotated dental treatment dataset is configured to deep learn dental treatment datasets.

A dental image, dental image landmark, a supervised and/or unsupervised annotated dental image anatomy dataset, a supervised and/or unsupervised annotated dental image pathology dataset, supervised and/or unsupervised dental image landmark dataset, a supervised and/or unsupervised annotated dental image landmark dataset, a supervised and/or unsupervised annotated dental treatment dataset, an annotated dental treatment dataset may be merged with an individual information dataset and processed with a deep neural network to produce an artificial intelligence dental image dataset.

An artificial intelligence dental image dataset may match and identify a supervised and/or unsupervised annotated dental treatment dataset with an individual information dataset to generate multiple treatment options and/or treatment plans for at least one of a dental professional, a health care professional, an individual, e-commerce organization.

An annotated dental product dataset may be correlated and/or merged with an artificial intelligence dental image dataset. The annotated dental product dataset may be annotated by at least one of a dental provider, a health care professional, an individual, an e-commerce organization, a researcher, a manufacturer, an artificial intelligence mechanism, an artificial intelligence dental dataset.

The annotated dental product dataset may be merged to an artificial intelligence dental dataset and compared to a supervised and/or unsupervised annotated dental image landmark dataset to produce multiple treatment options with dental product recommendations and/or treatment options and no product recommendations of a dental image landmark. Further, the multiple treatment options with product recommendations and/or no treatment options and no product recommendations may be associated with a treatment confidence score and/or a dental product confidence score to produce reward training and/or a transfer learning value(s) for the artificial intelligence dental dataset. The confidence score, rewards training and/or transfer learning of multiple treatment options with product recommendations and/or no treatment options and no product recommendations may be provided to at least one of a dental professional, a health care professional, an individual, e-commerce organization.

An example of a dental product recommendation may include recommending a specific orthodontic aligner and/or a manufacturer for orthodontic aligner fabrication.

Another example of a dental product recommendation may include a specific dental implant and/or a specific dental implant size for a dental image. Dental product recommendation may include at least one of a specific orthodontic aligner, a specific dental implant, a specific crown, a specific membrane, a specific graft, a specific screw, a specific composite, a specific amalgam, a specific dental instrument to a dental professional, a health care professional, an individual, an e-commerce organization. A further example may include recommending a specific brand of dental crown and or a specific dental laboratory.

The disclosed system comprises an aggregator server configured to represent at least one of a dental image, a dental image landmark, a supervised and/or unsupervised dental image landmark dataset, a supervised and/or unsupervised annotated dental image landmark dataset, a supervised and/or unsupervised annotated dental treatment dataset, an annotated dental treatment dataset, an artificial intelligence dental image dataset, an annotated diagnostic treatment aid, an annotated treatment demonstration aid, an annotated diagnostic treatment aid and/or annotated treatment demonstration aid represented and displayed as at least one of a number, a percentage, a percent, a proportion, a ratio, a graph, a color, an image, a score, a grade, a count, a rate, an average, a figure, an outline, an area, a shading. Further, the aggregator server configured to execute an aggregator service to exchange at least one of a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, annotated dental image treatment dataset, an artificial intelligence dental dataset, an individual information dataset with a client device, wherein a client devise includes a server, a desktop computer, a workstation, a laptop computer, a cell phone, a tablet, a mobile device, a cloud-based storage service.

A dental professional and/or a health professional may use a dental image, a dental image landmark, a supervised and/or unsupervised dental image landmark dataset, an supervised and/or unsupervised annotated dental image landmark dataset, a supervised and/or unsupervised annotated dental treatment dataset, an annotated dental treatment dataset, an artificial intelligence dental image dataset, an annotated diagnostic treatment aid, an annotated treatment demonstration aid, an annotated diagnostic treatment aid and/or annotated treatment demonstration aid to an individual.

At least one of a dental professional, a health professional, an individual, a deep learning mechanism may process a transaction of at least one of an exchange, a transfer, a purchase, a sell of at least one of a dental image, a dental image landmark, a supervised and/or unsupervised dental image landmark dataset, a supervised and/or unsupervised annotated dental image landmark dataset, a supervised and/or unsupervised annotated dental treatment dataset, an annotated dental treatment dataset, an artificial intelligence dental image dataset, an individual information dataset over a communication network such as the internet, wherein a communication network includes at least one of the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

Further, a processor configured for a dental professional and/or an individual to process a transaction of at least one of an exchange, a transfer, a buy, a sell of at least one of a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, a supervised and/or unsupervised annotated dental treatment dataset, an annotated dental image treatment dataset, an artificial intelligence dental image dataset, an individual information dataset in exchange for at least one of a currency, data, a discount, a product, goods, a software, an application, an advertisement.

The artificial intelligence dental may compare treatment success and produce a treatment confidence score based on patient compliance factors which may include at least one of number individual visits, number of broken appointments, failure to complete treatment rate, an ASA grade, a smoker, a diabetic, a biologic medication and provide to a dental professional, a health professional, an individual, an e-commerce organization.

An aggregator server may use an artificial intelligence mechanism to process a dental image, a dental image landmark, a dataset with natural language processing. Wherein a dataset includes at least one of a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, an annotated dental image treatment dataset, an artificial intelligence dental dataset, an individual information dataset.

Referring now to figures, FIG. 1 is an illustration of an online platform 100 consistent with various embodiments of the present invention. By way of non-limiting example, the online platform 100 to facilitate generation of a dental recommendation based on image processing may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers etc.), databases 114, sensors 116, over a communication network 104, such as, but not limited to, the Internet. Further, users of the online platform 100 may include relevant parties such as, but not limited to, end users, and administrators. Accordingly, in some instances, electronic devices operated by the one or more relevant parties may be in communication with the online platform 100.

A user 112, such as the one or more relevant parties, may access the online platform 100 through a web based software application or browser. The web based software application may be embodied as, for example, but not be limited to, a website, a web application, a desktop application, and a mobile application compatible with a computing device 1200.

Figure 2:
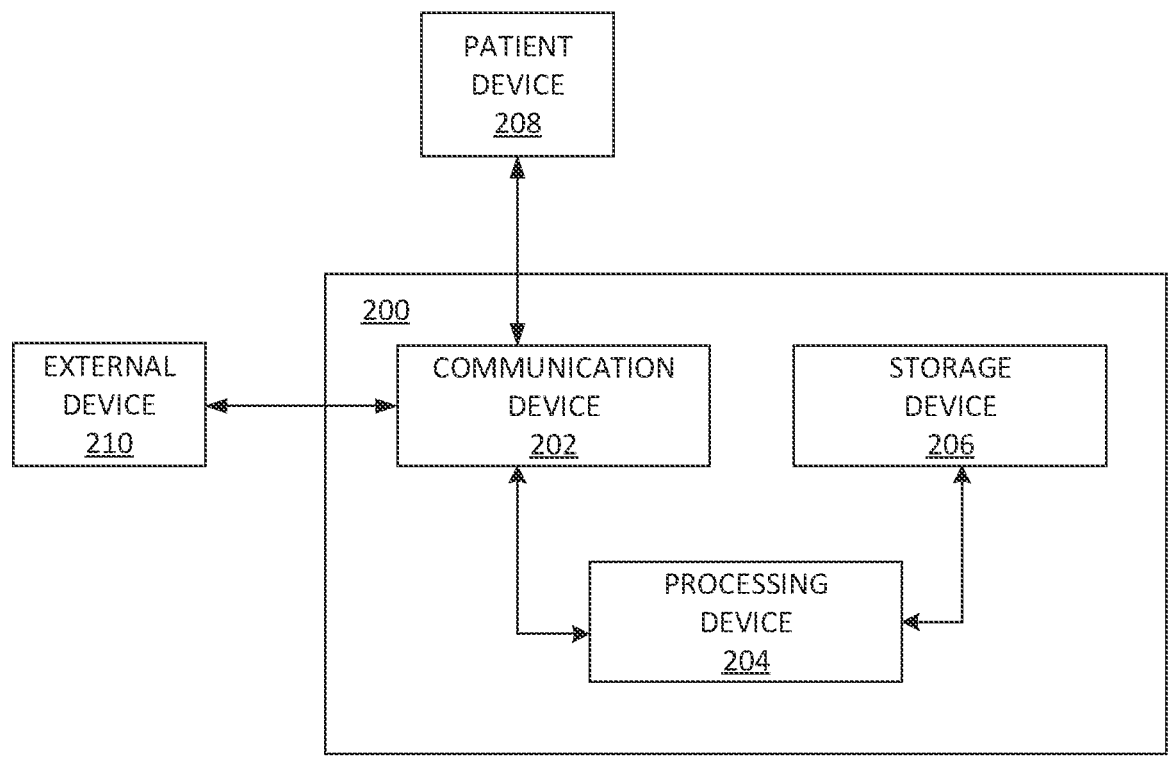
FIG. 2 is a block diagram of a system for facilitating generating a dental recommendation based on image processing, in accordance with some embodiments.

FIG. 2 is a block diagram of a system 200 for generating a dental recommendation based on image processing, in accordance with some embodiments. Accordingly, the system 200 may include a communication device 202, a processing device 204 and a storage device 206.

Further, the communication device 202 may be configured for receiving at least one patient data comprising at least one image from at least one patient device 208. Further, the communication device 202 may be configured for transmitting at least one dental recommendation to at least one external device 210. Further, the at least one patient data may include personal information associated with the at lea least one patient data. Further, the personal information may include name, identification number, address, contact information, medical history, etc. Further, the at least one patient device 208 may include at least one user device and at least
- one diagnosis device, wherein the at least one user device is associated with at least one patient, wherein the at least one diagnosis device is configured for generating a diagnosing data. Further, the at least one user device may include a smartphone, a tablet, a mobile device, a computer, a laptop, and so on. Further, the at least one diagnosing device may include an x-ray, a camera, an image capturing device, toothbrush with imaging device,
- toothbrush with imaging device a being camera, an intraoral scanner, a magnetic resonance image (MRI) device, a computed tomography (CT) scan equipment, cone beam computed tomography device, and so on. Further, in some embodiments, the at least one external device 210 may be associated with the at least one patient device 208. Further, the at least one external device 210 may include a smartphone, a tablet, a mobile, a personal computer, a laptop, and so on. Further, in some embodiments, the at least one external device 210 may be associated with a second user. Further, the second user may include a healthcare professional, dental professional, government organization, e-commerce provider, etc.

Further, the processing device 204 may be configured for analyzing the at least one patient data and at least one dental dataset. Further, the at least one dental dataset may be associated with the at least one patient data. Further, the at least one dental dataset may include a classified dental image dataset. Further, the classified dental image dataset may include at least one of a classified dental image anatomy dataset and a classified dental image pathology dataset.

In some embodiments, the analyzing of the at least one patient data and the at least one dental dataset may be based on at least one first artificial intelligence model. Further, the at least one first artificial intelligence model may be configured for identifying of the at least one dental characteristic associated with the at least one patient data.

Further, the processing device 204 may be configured for generating at least one landmark based on the analyzing. Further, the at least one landmark comprises at least one dental characteristic associated with the at least one patient data.

Further, the processing device 204 may be configured for processing the at least one landmark and at least one dental reference dataset. Further, the processing device 204 may be configured for determining the at least one dental recommendation based on the processing.

In some embodiments, the processing of the at least one landmark and the at least one dental reference may be based on at least one second artificial intelligence model. Further, the at least one second artificial intelligence model may be configured for determining of the at least one dental recommendation.

Further, the storage device 206 may be configured for retrieving the at least one dental dataset, retrieving the at least one dental reference dataset and storing the at least one dental recommendation.

According to some embodiments, the at least one external device 210 may include at least one first user device associated with at least one first user. Further, the at least one first user may include a dental professional, a healthcare professional, e-commerce service vendor, etc. Further, the at least one first user device may include a smartphone, a tablet, a laptop, a personal computer, and so on. Further, the communication device 202 may be configured for transmitting a request to the at least one first user device of the at least one external device 210, receiving at least one first user data from the at least one first user device; and transmitting a notification to at least one of the at least one patient device 208 and the at least one external device 210. Further, the at least one first user data may include certifications, qualification proof, license number, etc. that may be verified. Further, the processing device 204 may be configured for analyzing the at least one first user data based on at least one regulatory data and generating the notification corresponding to the at least one first user based on the analyzing of the at least one first user data. Further, the storage device 206 may be configured for retrieving the at least one regulatory data based on the at least one first user.

According to some embodiments, the at least one dental recommendation may include a dental product recommendation and a dental treatment recommendation. Further, the communication device 202 may be configured for transmitting the at least one dental recommendation and the at least one patient data to at least one expert device associated with at least one expert. Further, the at least one expert may include a dental professional, a healthcare professional, etc. Further, the communication device 202 may be configured for receiving a first confidence score from the at least one expert device. Further, the first confidence score may be associated with the at least one dental recommendation. Further, the communication device 202 may be configured for transmitting the first confidence score to the at least one external device 210. Further, the first confidence score may include a measure of appreciation. Further, the first confidence score may include a rating, a score, etc. Further, the at least one expert device may include a smartphone, a tablet, a laptop, a personal computer, and so on.

According to further embodiments, the processing device 204 may be configured for updating the at least one dental reference dataset with the at least one patient data and the at least one dental recommendation based on the first confidence score and generating at least one updated reference dataset based on the updating of the at least one dental reference dataset. Further, the storage device 206 may be configured for storing the at least one updated reference dataset.

According to further embodiments, the communication device 202 may be configured for receiving an order from the at least one patient device 208. Further, the order may be associated with the at least one dental recommendation, transmitting the order to the at least one external device 210, receiving a response corresponding to the order from the at least one external device 210 and transmitting the response to the at least one patient device 208.

According to further embodiments, the communication device 202 may be configured for transmitting the at least one patient data and the at least one landmark to the at least one expert device, receiving a second confidence score from the at least one expert device. Further, the second confidence score may be associated with the at least one landmark and transmitting the second confidence score to the at least one external device 210.

According to further embodiments, the communication device 202 may be configured for transmitting a validity notification to the at least one external device 210. Further, the processing device 204 may be configured for analyzing the at least one patient data and the at least one dental dataset and generating the validity notification corresponding to the at least one patient data based on the analyzing. Further, the validity notification may be associated with a measure of approval of the at least one patient data.

Figure 3:
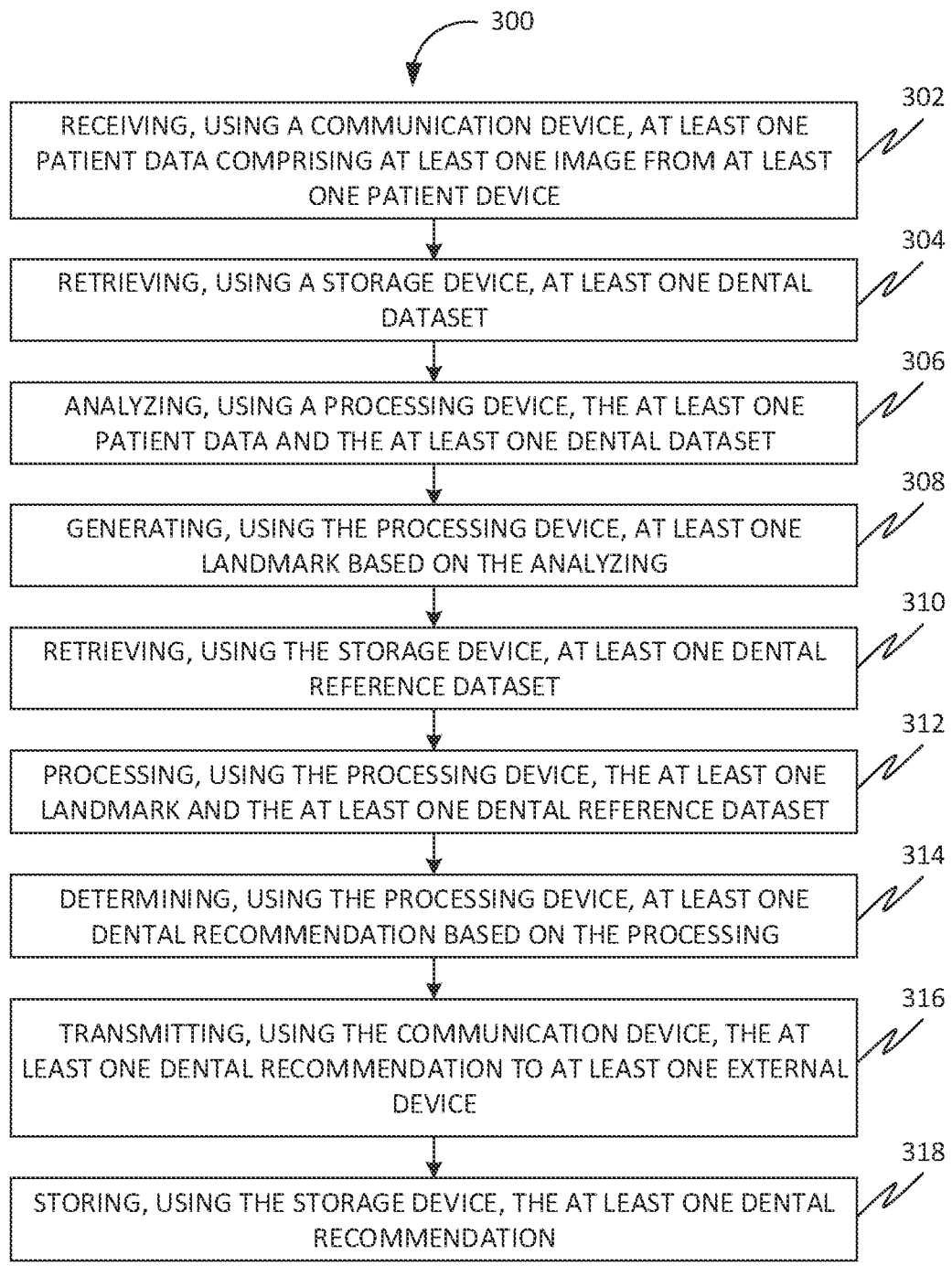
FIG. 3 is a flowchart of a method of generating a dental recommendation based on image processing, in accordance with some embodiments.

FIG. 3 is a flowchart of a method 300 of generating a dental recommendation based on image processing, in accordance with some embodiments. At 302, the method 300 may include receiving, using a communication device, at least one patient data comprising at least one image from at least one patient device. Further, the at least one patient data may include personal information associated with the at lea least one patient data. Further, the personal information may include name, identification number, address, contact information, medical history, etc. Further, the at least one patient device may include at least one user device and at least one diagnosis device, wherein the at least one user device is associated with at least one patient, wherein the
 at least one diagnosis device is configured for generating a diagnosing data. Further, the at least one user device may include a smartphone, a tablet, a mobile device, a personal computer, a laptop, and so on. Further, the at least one diagnosing device may include an x-ray, a camera, an image capturing device, toothbrush with imaging device, toothbrush with imaging device a being camera, an intraoral scanner, a magnetic resonance image (MRI) device, a computed
tomography (CT) scan equipment, cone beam computed tomography device, and so on.

Further, at 304, the method 300 may include retrieving, using a storage device, at least one dental dataset.

Further, at 306, the method 300 may include analyzing, using a processing device, the at least one patient data and the at least one dental dataset. Further, the at least one dental dataset is associated with the at least one patient data. Further, the at least one dental dataset comprises a classified dental image dataset. According to some embodiments, the classified dental image dataset may include at least one of a classified dental image anatomy dataset and a classified dental image pathology dataset.

According to some embodiments, the analyzing of the at least one patient data and the at least one dental dataset may be based on at least one first artificial intelligence model. Further, at least one first artificial intelligence model may be configured for identifying of the at least one dental characteristic associated with the at least one patient data Further, at 308, the method 300 may include generating, using the processing device, at least one landmark based on the analyzing. Further, the at least one landmark comprises at least one dental characteristic associated with the at least one patient data.

Further, at 310, the method 300 may include retrieving, using the storage device, at least one dental reference dataset.

Further, at 312, the method 300 may include processing, using the processing device, the at least one landmark and the at least one dental reference dataset.

According to some embodiments, the processing of the at least one landmark and the at least one dental reference dataset may be based on at least one second artificial intelligence model, wherein the at least one second artificial intelligence model is configured for determining of the at least one dental recommendation.

Further, at 314, the method 300 may include determining, using the processing device, at least one dental recommendation based on the processing.

Further, at 316, the method 300 may include transmitting, using the communication device, the at least one dental recommendation to at least one external device. Further, in some embodiments, the at least one external device may be associated with the at least one patient device. Further, the at least one external device may include a smartphone, a tablet, a mobile, a personal computer, a laptop, and so on. Further, in some embodiments, the at least one external device may be associated with a second user. Further, the second user may include a healthcare professional, dental professional, government organization, e-commerce provider, etc.

Further, at 318, the method 300 may include storing, using the storage device, the at least one dental recommendation.

Figure 4:
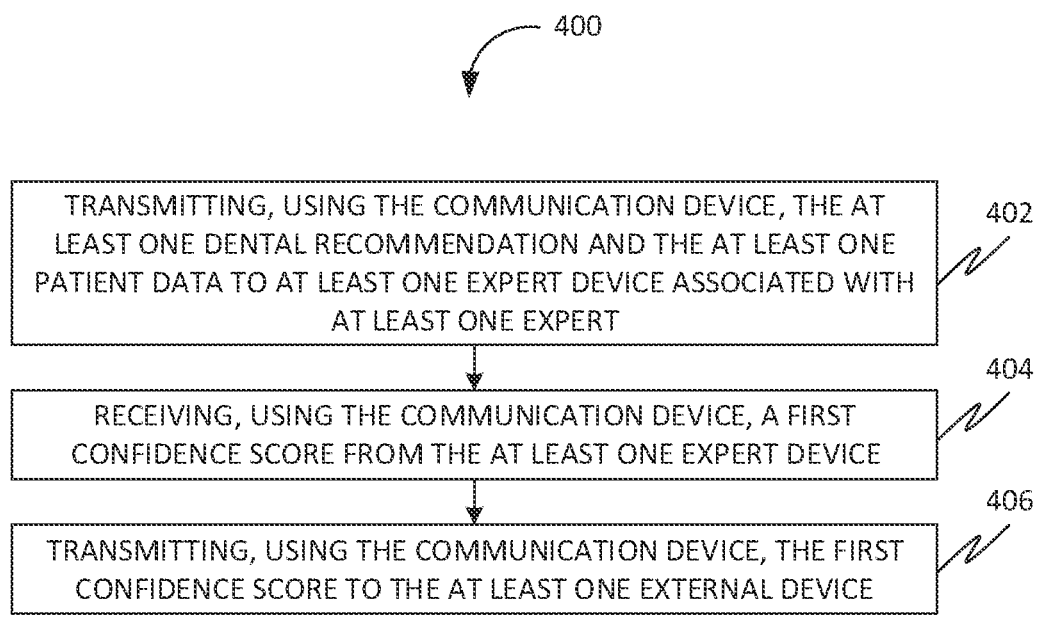
FIG. 4 is a flowchart of a method of obtaining a first confidence score associated with the at least one dental recommendation, in accordance with some embodiments.

FIG. 4 is a flowchart of a method 400 of obtaining a first confidence score associated with the at least one dental recommendation, in accordance with some embodiments. Further, the at least one dental recommendation may include a dental product recommendation and a dental treatment recommendation.

At 402, the method 400 may include transmitting, using the communication device, the at least one dental recommendation and the at least one patient data to at least one expert device associated with at least one expert. Further, the at least one expert may include a dental professional, a healthcare professional, etc.

Further, at 404, the method 400 may include receiving, using the communication device, the first confidence score from the at least one expert device. Further, the first confidence score may include a measure of appreciation. Further, the first confidence score may include a rating, a score, etc.

Further, at 406, the method 400 may include transmitting, using the communication device, the first confidence score to the at least one external device.

Figure 5:
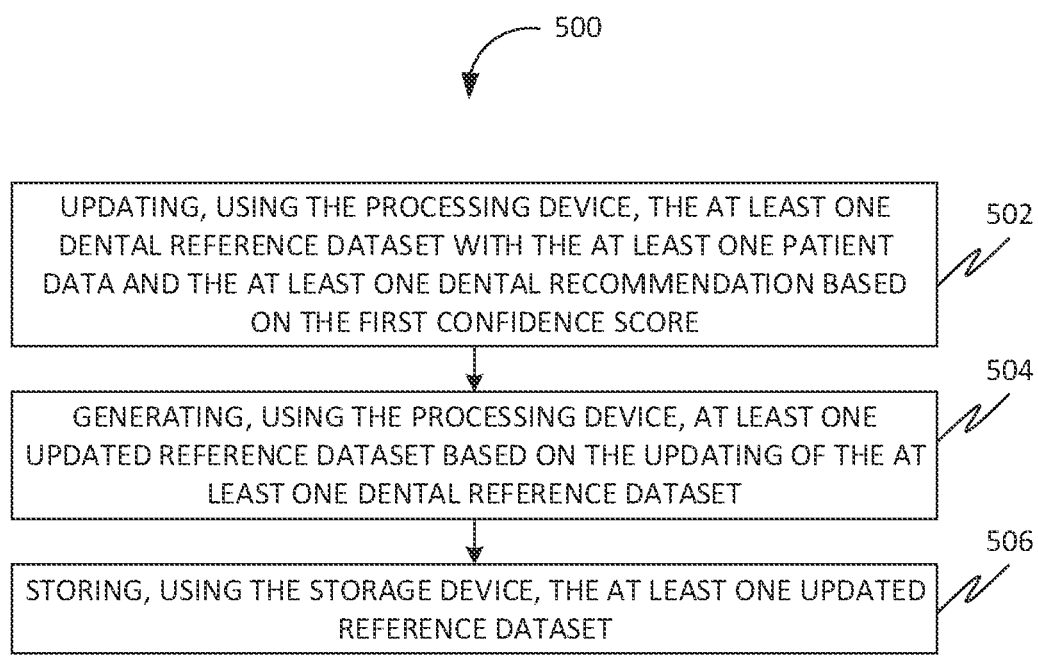
FIG. 5 is a flowchart of a method of obtaining at least one updated reference dataset, in accordance with some embodiments.

FIG. 5 is a flowchart of a method 500 of obtaining at least one updated reference dataset, in accordance with some embodiments.

At 502, the method 500 may include updating, using the processing device, the at least one dental reference dataset with the at least one patient data and the at least one dental recommendation based on the first confidence score.

Further, at 504, the method 500 may include generating, using the processing device, the at least one updated reference dataset based on the updating of the at least one dental reference dataset.

Further, at 506, the method 500 may include storing, using the storage device, the at least one updated reference dataset.

Figure 6:
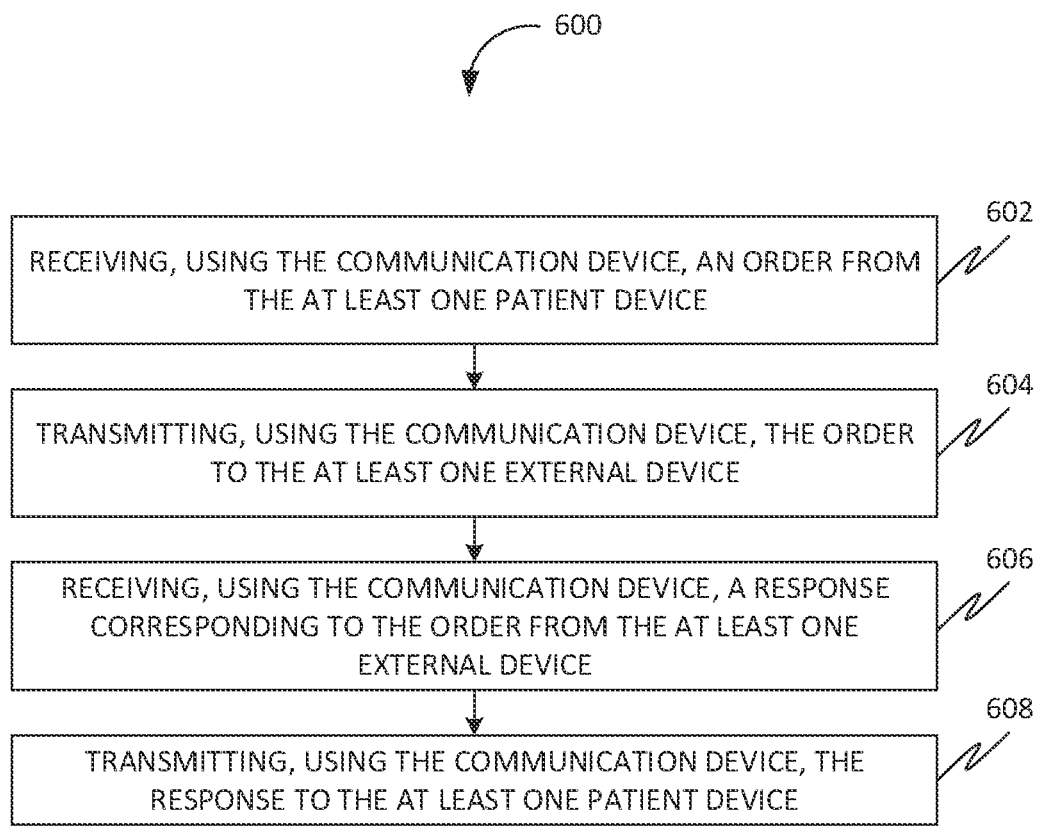
FIG. 6 is a flowchart of a method of processing an order, in accordance with some embodiments.

FIG. 6 is a flowchart of a method 600 of processing an order, in accordance with some embodiments. Further, the order may be associated with the at least one dental recommendation. Further, at 602, the method 600 may include receiving, using the communication device, the order from the at least one patient device.

Further, at 604, the method 600 may include transmitting, using the communication device, the order to the at least one external device.

Further, at 606, the method 600 may include receiving, using the communication device, a response corresponding to the order from the at least one external device.

Further, at 608, the method 600 may include transmitting, using the communication device, the response to the at least one patient device.

Figure 7:
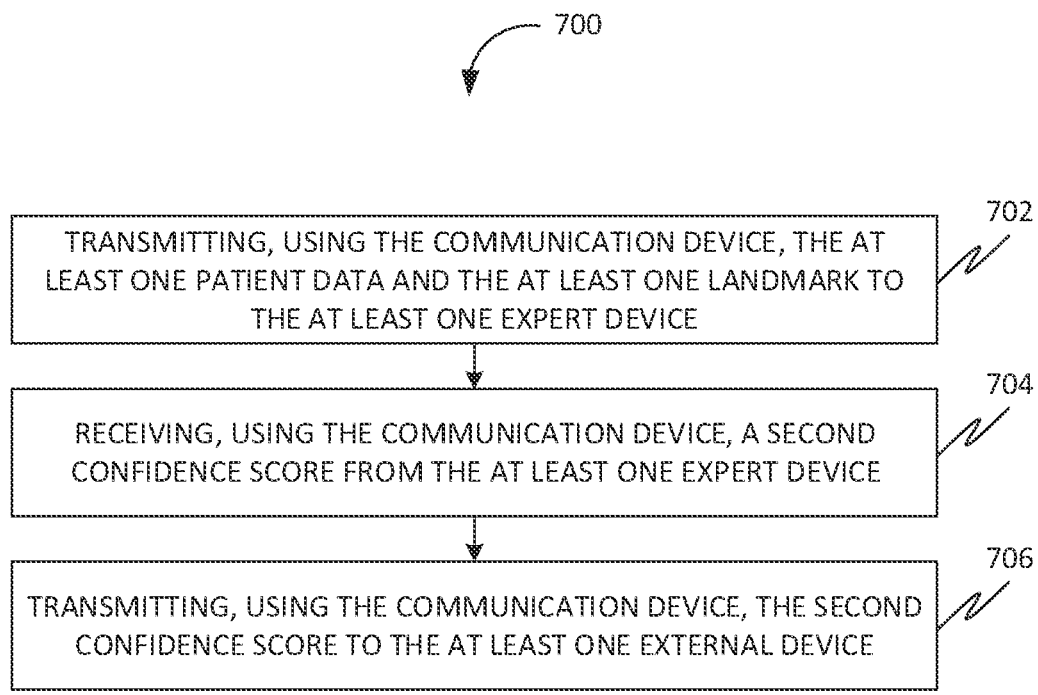
FIG. 7 is a flowchart of a method of obtaining a second confidence score associated with the at least one landmark, in accordance with some embodiments.

FIG. 7 is a flowchart of a method 700 of obtaining a second confidence score associated with the at least one landmark, in accordance with some embodiments. At 702, the method 700 may include transmitting, using the communication device, the at least one patient data and the at least one landmark to the at least one expert device.

Further, at 704, the method 700 may include receiving, using the communication device, a second confidence score from the at least one expert device. Further, the second confidence score may include a measure of appreciation. Further, the second confidence score may include a rating, a score, etc.

Further, at 706, the method 700 may include transmitting, using the communication device, the second confidence score to the at least one external device.

Figure 8:
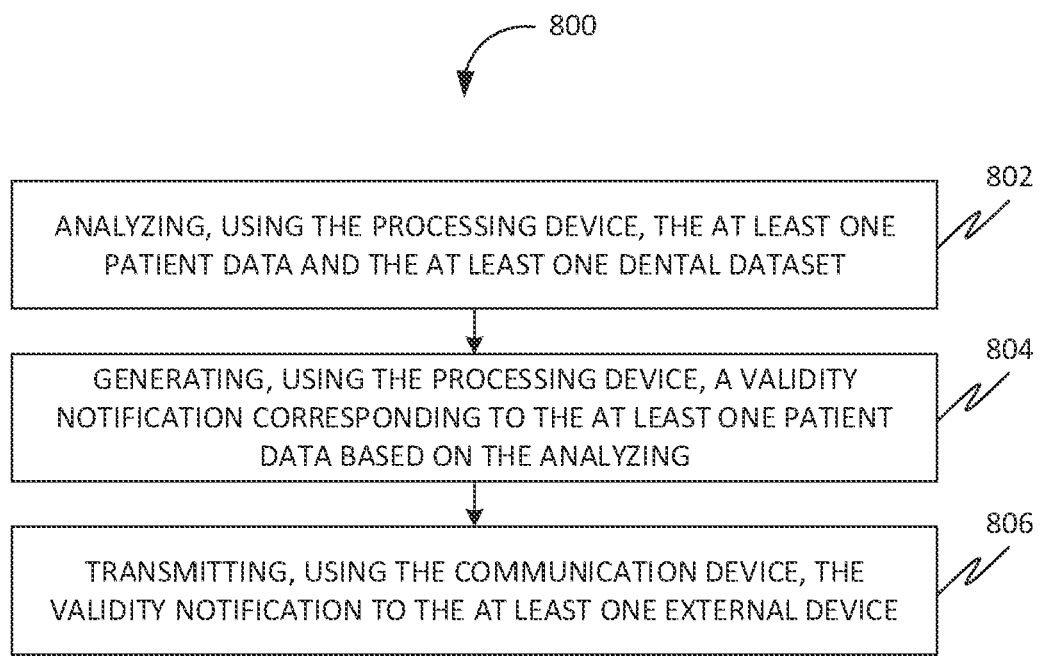
FIG. 8 is a flowchart of a method of obtaining a validity notification corresponding to the at least one patient data, in accordance with some embodiments.

FIG. 8 is a flowchart of a method 800 of obtaining a validity notification corresponding to the at least one patient data, in accordance with some embodiments.

Further, at 802, the method 800 may include analyzing, using the processing device, the at least one patient data and the at least one dental dataset.

Further, at 804, the method 800 may include generating, using the processing device, the validity notification corresponding to the at least one patient data based on the analyzing. Further, the validity notification may be associated with a measure of approval of the at least one patient data.

Further, at 806, the method 800 may include transmitting, using the communication device, the validity notification to the at least one external device.

Figure 9:
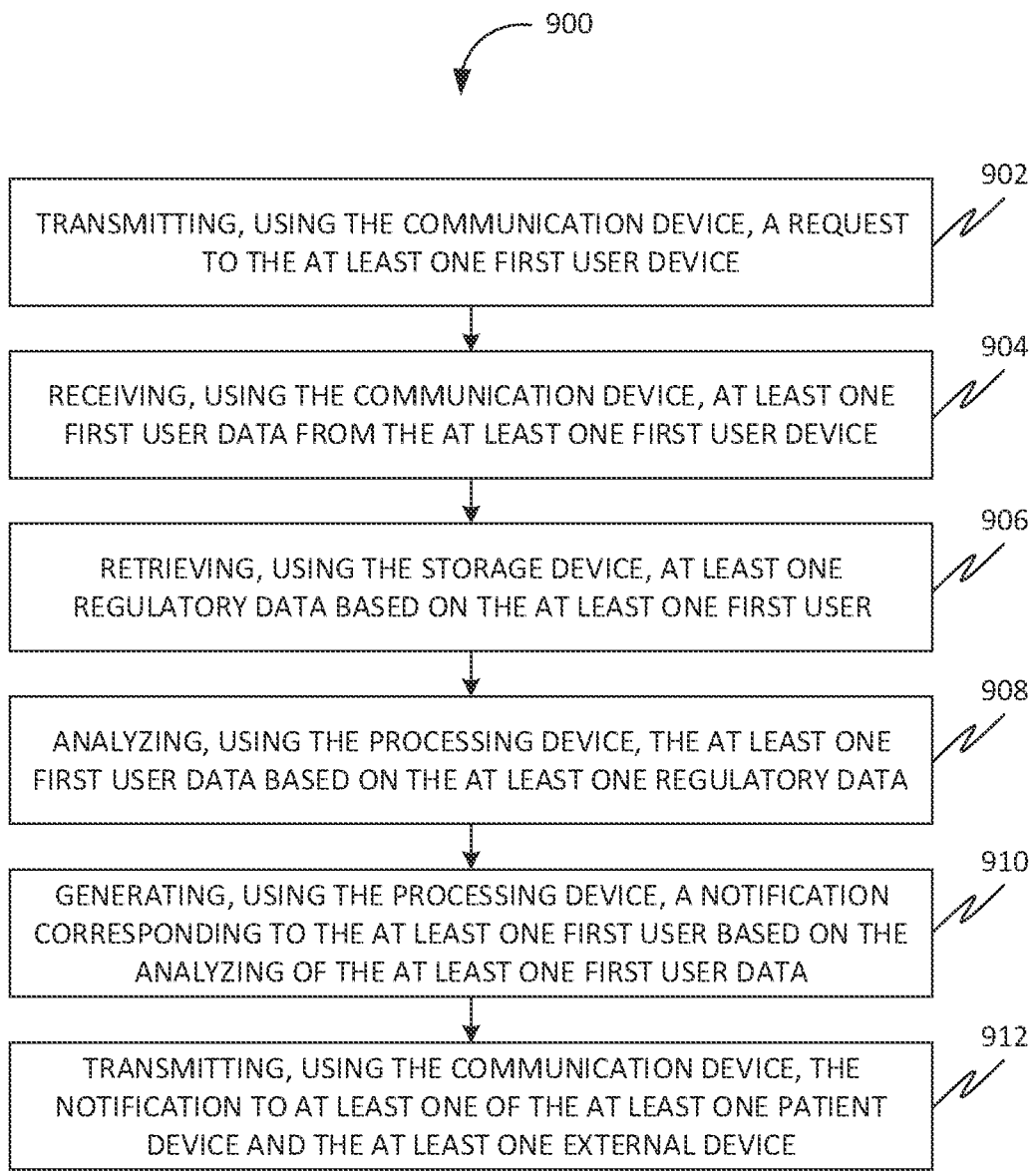
FIG. 9 is a flowchart of a method of obtaining a notification corresponding to the at least one first user, in accordance with some embodiments.

FIG. 9 is a flowchart of a method 900 of obtaining a notification corresponding to the at least one first user, in accordance with some embodiments. Further, the at least one external device may include at least one first user device associated with at least one first user At 902, the method 900 may include transmitting, using the communication device, a request to the at least one first user device.

Further, at 904, the method 900 may include receiving, using the communication device, at least one first user data from the at least one first user device. Further, the at least one first user device may include a smartphone, a tablet, a laptop, a personal computer, and so on. Further, the at least one first user data may include certifications, qualification proof, license number, etc. that may be verified. Further, the at least one first user may include a dental professional, a healthcare professional, e-commerce service vendor, etc.

Further, at 906, the method 900 may include retrieving, using the storage device, at least one regulatory data based on the at least one first user.

Further, at 908, the method 900 may include analyzing, using the processing device, the at least one first user data based on the at least one regulatory data.

Further, at 910, the method 900 may include generating, using the processing device, a notification corresponding to the at least one first user based on the analyzing of the at least one first user data.

Further, at 912, the method 900 may include transmitting, using the communication device, the notification to at least one of the at least one patient device and the at least one external device.

Further, in some embodiments, the method for determining a dental recommendation based on location is disclosed. Accordingly, the at least one patient data comprises a location data. Accordingly, the method may include a step of analyzing, using the processing device, the location data and the at least one dental recommendation.

Further, the method may include a step of determining, using the processing device, a first dental recommendation of the at least one dental recommendation based on the analyzing of the location data and the at least one dental recommendation; and Further, the method may include a step of transmitting, using the communication device, the first dental recommendation to the at least one external device.

Figure 10:
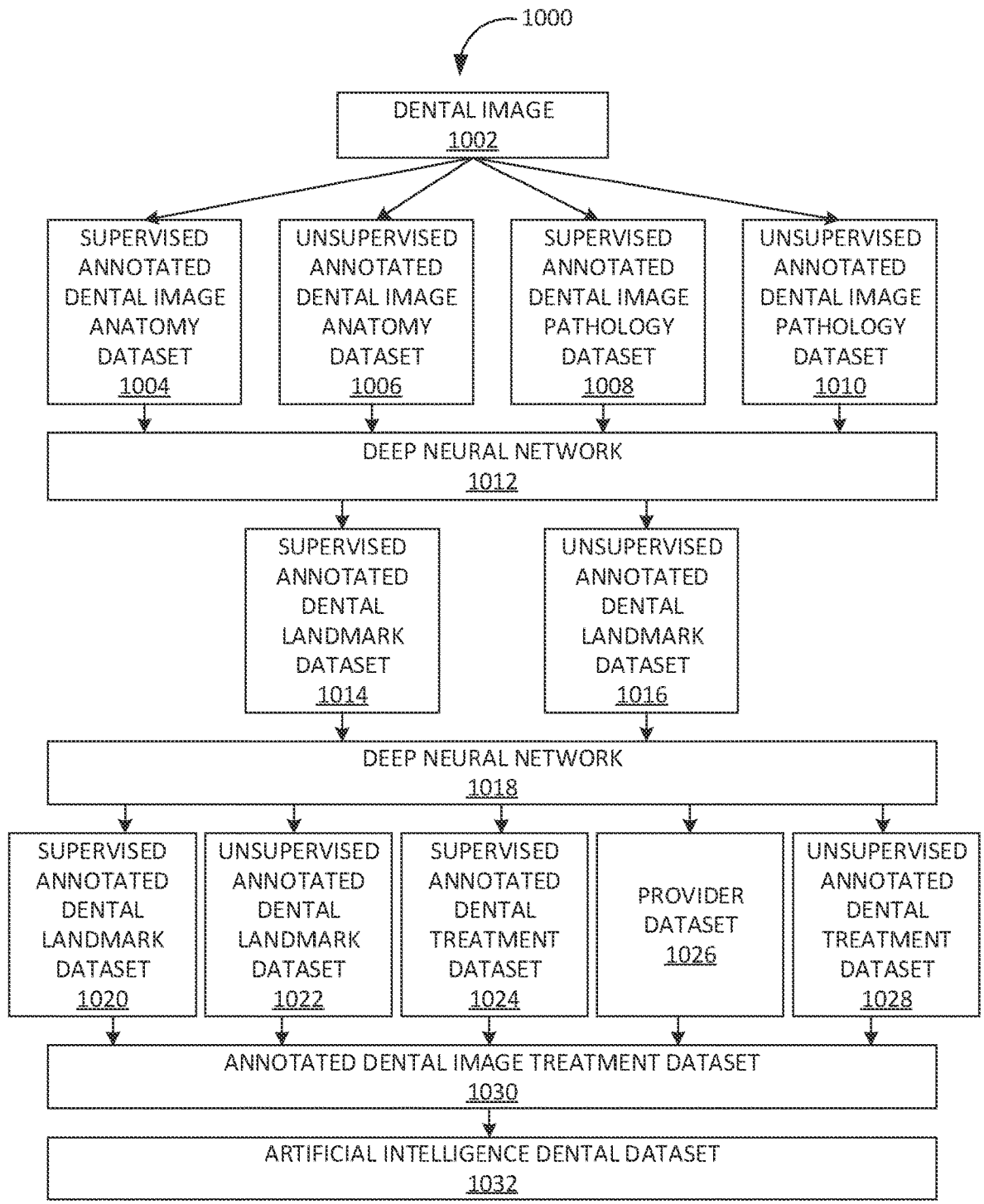
FIG. 10 is a flow diagram of a method for facilitating matching and identifying a dental image with a supervised and/or unsupervised annotated deep neural network to produce an artificial intelligence dental dataset, in accordance with some embodiments.

FIG. 10 is a flow diagram of a method 1000 for facilitating matching and identifying a dental image with a supervised and/or unsupervised annotated deep neural network to produce an artificial intelligence dental dataset, in accordance with some embodiments. At 1002, the method 1000 may include receiving a dental image.

At 1004, the method 1000 may include analyzing the dental image based on a supervised annotated dental image anatomy dataset.

At 1006, the method 1000 may include analyzing the dental image based on unsupervised annotated dental image anatomy dataset.

At 1008, the method 1000 may include analyzing the dental image based on supervised annotated dental image pathology dataset.

At 1010, the method 1000 may include analyzing the dental image based on unsupervised annotated dental image pathology dataset.

At 1012, the method 1000 may include processing the dental image based on a deep neural network.

At 1014, the method 1000 may include analyzing at least one of the dental image, the annotated dental image anatomy dataset and/or an annotated dental image pathology dataset based on a supervised annotated dental landmark dataset to produce a dental image landmark.

At 1016, the method 1000 may include analyzing at least one of the dental image, the annotated dental image anatomy dataset and/or an annotated dental image pathology dataset based on an unsupervised annotated dental landmark dataset to produce a dental image landmark.

At 1018, the method 1000 may include processing the dental image with the dental image landmark based on the deep neural network.

At 1020, the method 1000 may include analyzing the dental image with the dental image landmark based on supervised annotated dental landmark dataset.

At 1022, the method 1000 may include analyzing the dental image with the dental image landmark based on unsupervised annotated dental landmark dataset.

At 1024, the method 1000 may include analyzing the dental image with the dental image landmark based on supervised annotated dental treatment dataset.

At 1026, the method 1000 may include analyzing the dental image with the dental image landmark based on provider dataset.

At 1028, the method 1000 may include analyzing the dental image with the dental image landmark based on unsupervised annotated dental treatment dataset.

At 1030, the method 1000 may include analyzing the dental image landmark of the dental image based on annotated dental image treatment dataset. Further, the annotated dental image treatment dataset may include a supervised annotated dental image treatment dataset and an unsupervised annotated dental image treatment dataset. Further, the supervised and/or unsupervised annotated dental treatment dataset may match and identify the dental image landmark of the dental image and provide treatment recommendations and/or no treatment recommendations for the dental image landmark. Further, the dental image may be matched directly to the supervised and/or unsupervised annotated dental treatment dataset.

At 1032, the method 1000 may include merging the dental image, the dental image landmark, the supervised and/or unsupervised annotated dental image anatomy dataset, the supervised and/or unsupervised annotated dental image pathology dataset, the supervised and/or unsupervised dental image landmark dataset, the supervised and/or unsupervised annotated dental image landmark dataset, the supervised and/or unsupervised annotated dental treatment dataset, the annotated dental treatment dataset with an individual information dataset and processed with the deep neural network to produce an artificial intelligence dental image dental dataset.

Figure 11:
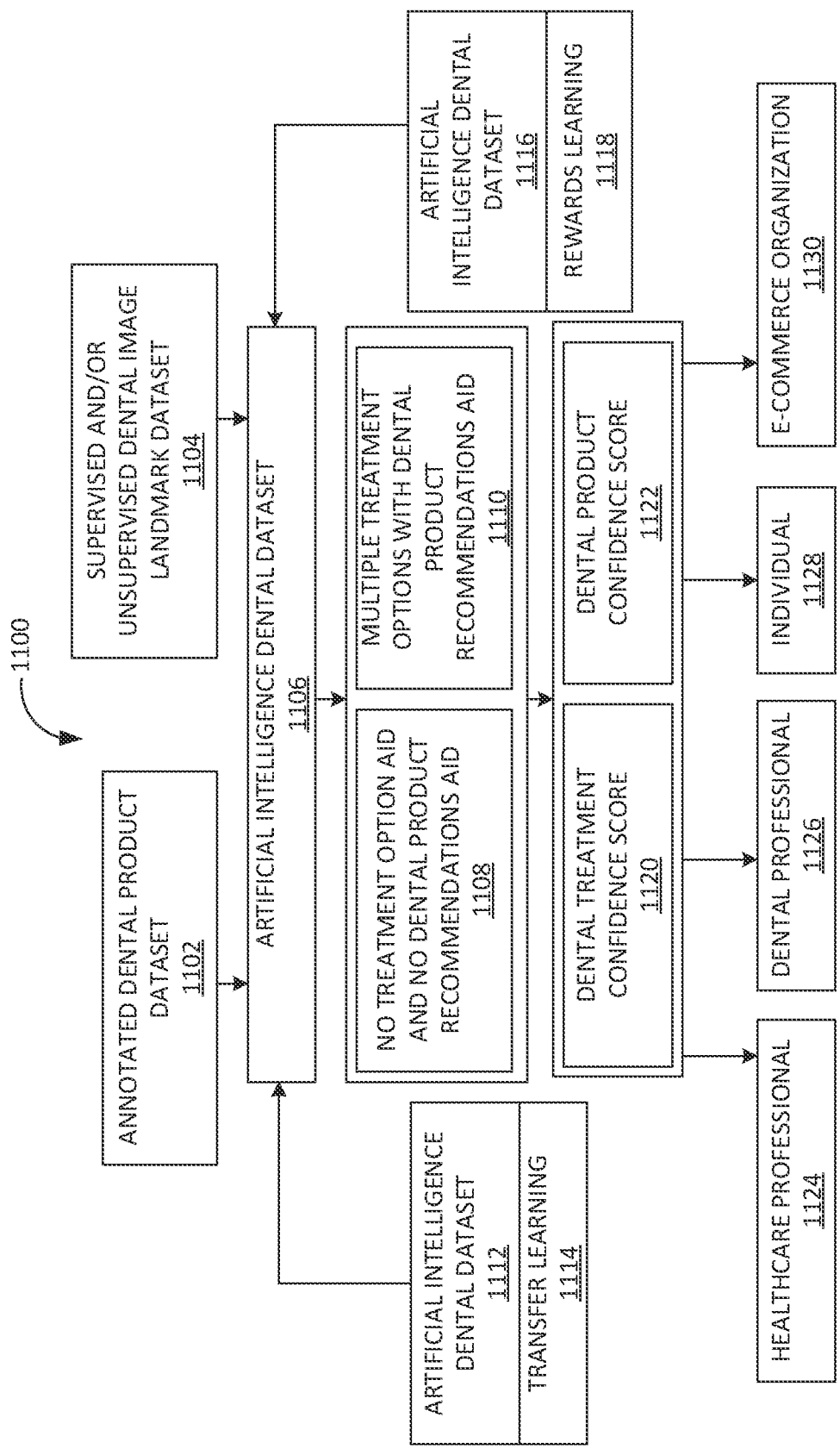
FIG. 11 is a flow diagram of a method for facilitating identifying treatment options and/or no treatment option recommendation with dental product recommendations with dental treatment and/or dental product confidence scores based on analyzing a supervised and/or unsupervised dental image landmark dataset using an artificial intelligence mechanism, in accordance with some embodiments.

FIG. 11 is a flow diagram of a method 1100 for facilitating identifying treatment options and/or no treatment option recommendation with dental product recommendations with dental treatment and/or dental product confidence scores based on analyzing a supervised and/or unsupervised dental image landmark dataset using an artificial intelligence mechanism, in accordance with some embodiments. Accordingly, at 1102, the method 1100 may include receiving an annotated dental product dataset.

At 1104, the method 1100 may include receiving a supervised and/or unsupervised dental image landmark dataset.

At 1106, the method 1100 may include merging the annotated dental product dataset and the supervised and/or unsupervised dental image landmark dataset to produce an artificial intelligence dental dataset.

At 1108, the method 1100 may include generating no treatment option aid and no dental product recommendations aid based on the artificial intelligence dental dataset.

At 1110, the method 1100 may include generating multiple treatment options with dental product recommendations aid.

At 1112, the method 1100 may include storing learning values in the artificial intelligence dental dataset.

At 1114, the method 1100 may include generating the learning values associated with multiple treatment options with dental product based on a dental treatment confidence score and a dental product confidence score.

At 1116, the method 1100 may include storing a reward learning in the artificial intelligence dental dataset.

At 1118, the method 1100 may include generating rewards learning based on the dental treatment confidence score and the dental product confidence score.

At 1120, the method 1100 may include generating the dental treatment confidence score.

At 1122, the method 1100 may include generating the dental product confidence score.

At 1124, the method 1100 may include transmitting at least one of the multiple treatment options with dental product recommendations aid, the reward training, the learning value, the dental treatment confidence score and the dental product confidence score to a healthcare professional.

At 1126, the method 1100 may include transmitting at least one of the multiple treatment options with dental product recommendations aid, the reward training, the learning value, the dental treatment confidence score and the dental product confidence score to a dental professional.

At 1128, the method 1100 may include transmitting at least one of the multiple treatment options with dental product recommendations aid, the reward training, the learning value, the dental treatment confidence score and the dental product confidence score to an individual.

At 1130, the method 1100 may include transmitting at least one of the multiple treatment options with dental product recommendations aid, the reward training, the learning value, the dental treatment confidence score and the dental product confidence score to an e-commerce organization.

Figure 12:
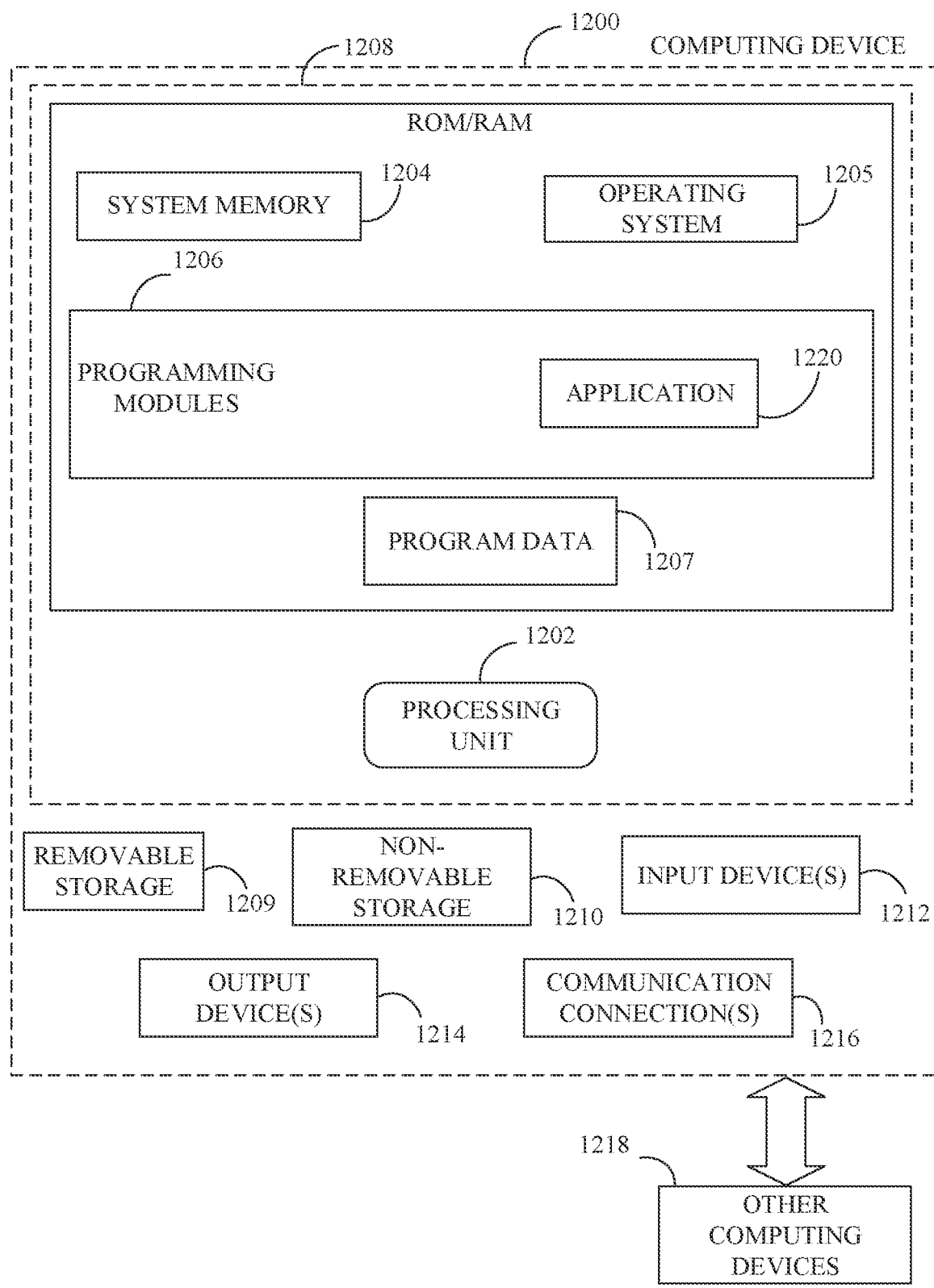
FIG. 12 is a block diagram of a computing device for implementing the methods disclosed herein, in accordance with some embodiments.

With reference to FIG. 12, a system consistent with an embodiment of the invention may include a computing device or cloud service, such as a computing device 1200. In a basic configuration, computing device 1200 may include at least one processing unit 1202 and a system memory 1204. Depending on the configuration and type of computing device, system memory 1204 may comprise, but is not limited to, volatile (e.g. random-access memory (RAM)), non-volatile (e.g. read-only memory (ROM)), flash memory, or any combination. System memory 1204 may include operating system 1205, one or more programming modules 1206, and may include a program data 1207. Operating system 1205, for example, may be suitable for controlling computing device 1200's operation. In one embodiment, programming modules 1206 may include image-processing module, machine learning module. Furthermore, embodiments of the invention may be practiced in conjunction with a graphics library, other operating systems, or any other application program and is not limited to any particular application or system This basic configuration is illustrated in FIG. 12 by those components within a dashed line 1208.

Computing device 1200 may have additional features or functionality. For example, computing device 1200 may also include additional data storage devices (removable and/or non-removable) such as, for example, magnetic disks, optical disks, or tape. Such additional storage is illustrated in FIG. 12 by a removable storage 1209 and a non-removable storage 1210. Computer storage media may include volatile and non-volatile, removable and non-removable media implemented in any method or technology for storage of information, such as computer-readable instructions, data structures, program modules, or other data. System memory 1204, removable storage 1209, and non-removable storage 1210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1200. Any such computer storage media may be part of device 1200. Computing device 1200 may also have input device(s) 1212 such as a keyboard, a mouse, a pen, a sound input device, a touch input device, a location sensor, a camera, a biometric sensor, etc. Output device(s) 1214 such as a display, speakers, a printer, etc. may also be included. The aforementioned devices are examples and others may be used.

Computing device 1200 may also contain a communication connection 1216 that may allow device 1200 to communicate with other computing devices 1218, such as over a network in a distributed computing environment, for example, an intranet or the Internet. Communication connection 1216 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 1204, including operating system 1205. While executing on processing unit 1202, programming modules 1206 (e.g., application 1220 such as a media player) may perform processes including, for example, one or more stages of methods, algorithms, systems, applications, servers, databases as described above. The aforementioned process is an example, and processing unit 1202 may perform other processes.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the invention, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present invention may be embodied in hardware and/or in software (including firmware, resident software, micro-code, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may, in fact, be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the invention.

Although the present invention has been explained in relation to its preferred embodiment, it is to be understood that many other possible modifications and variations can be made without departing from the spirit and scope of the invention.

Aspects

1. A system and process where dental images processed with artificial intelligence for e-commerce is described, the system comprising: an aggregator server, wherein the aggregator server is configured to:
   receive a dental image from at least one of: a dental professional, a health care provider, an individual, an e-commerce organization;
   train the aggregator server to match and identify a dental image to a supervised and/or unsupervised annotated dental image anatomy dataset and/or a supervised and/or unsupervised annotated dental image pathology dataset to produce a dental image landmark;
   train the aggregator server to process a dental image and/or a dental image landmark
with a deep neural network at one and/or multiple resolutions and match and identify to a supervised and/or unsupervised dental image landmark dataset;
   train the aggregator server to match and identify a dental image and/or a dental image landmark to a supervised and/or unsupervised dental image landmark dataset and match and identify to a supervised and/or unsupervised annotated dental image landmark dataset;
   train the aggregator server to match and identify a dental image and/or a dental image landmark to a supervised and/or unsupervised dental image landmark dataset and match to a supervised and/or unsupervised annotated dental treatment dataset;
   merge and identify at least one dental image and/or dental image landmark from a supervised and/or unsupervised annotated dental image landmark dataset to an annotated dental image treatment dataset;
   merge and identify at least one dental image and/or dental image landmark from a supervised and/or unsupervised annotated dental treatment dataset to an annotated dental image treatment dataset;
   an annotated dental image treatment dataset may be merged with an individual information dataset to produce an artificial intelligence dental dataset, wherein an individual information dataset includes at least one of an age, a first name, a gender, a middle initial, a last name, a date of birth, a zip code, an address, a cell phone number, a landline number, a current medication, a previous medication, a social security number, a marital status, an insurance, an insurance identification number, an email address, a change of insurance, a change of employment, a change of address, a change of zip code, a change of the previous medication, a change of the marital status, a change of gender;
   an annotated dental products dataset may be annotated by at least one of: a dental professional, a health care professional, an individual, an e-commerce organization, a researcher, a manufacturer, an artificial intelligence mechanism, an artificial intelligence dental dataset;
   an annotated dental product dataset may be matched to an artificial intelligence dental dataset to produce multiple treatment options with dental product recommendations and/or no treatment and/or no product recommendations for a dental image and/or a dental image landmark;
   a dental professional, a health care professional, an individual, an e-commerce organization may process a transaction of at least one of: an exchange, a transfer, a purchase, a sale of a dataset;
   wherein a dataset includes at least one of: a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, an annotated dental image treatment dataset, an artificial intelligence dental dataset, an individual information dataset over a communication network, wherein a communication network includes at least one of: the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

2. The aggregator server of claim 1, wherein the aggregator server is configured to process a transaction of at least one of: a dental image, a dental image landmark, a supervised and/or
unsupervised annotated dental image anatomy dataset, supervised and/or unsupervised annotated dental image pathology dataset, supervised and/or unsupervised dental image landmark dataset, a supervised and/or unsupervised annotated dental image landmark dataset, a supervised and/or unsupervised annotated dental treatment dataset, an annotated dental image treatment dataset, an artificial intelligence dental dataset, an individual information dataset, an annotated dental product dataset with at least one of: a dental professional, a health care professional, an individual, an e-commerce organization, wherein a transaction includes at least one of: business to business (B2B), business to consumer (B2C), consumer to business (C2B), consumer to consumer (C2C), business to administration (B2A), consumer to administration (C2A) transactions.

3. The aggregator server of claim 1, wherein the dental image is obtained from at least one of: a digital x-ray, a digital image, a cell phone captured image, a photographic image, a toothbrush with an imaging device, a toothbrush with an imaging device being a camera, a film based x-ray, a digitally scanned x-ray, a digitally captured x-ray, an intraoral scanner, a scintillator technology-based image, a trans-illumination image, a fluorescence technology-based image, a blue fluorescence technology-based image, a laser-based technology-based image, a magnetic resonance image (MRI), a computed tomography (CT) scan based image, a cone-beam computed tomography (CBCT) image.

4. The aggregator server of claim 1, wherein at least one of: a dental professional, a health care professional, an individual, an e-commerce organization utilizes an image capture device or a data storage device, and wherein the capture image device includes one or more of: an x-ray equipment, a digital camera, a cell phone camera, an intraoral scanner, a scintillator counter, an indirect or direct flat panel detector (FPD), a charged couple device (CCD), a phosphor plate radiography device, a picture archiving and communication system (PACS), a photo-stimulatable phosphor (PSP) device, a wireless complementary metal-oxide-semiconductor (CMOS) device.

5. The of claim 1, wherein the processing a dental image and/or a dental image landmark with at least one of:
   a sliding window component configured to analyze a dental image and/or a dental image landmark;
   a multiple grid component to divide and analyze a dental image and/or a dental image landmark;
   a bounding box component configured to analyze a dental image and/or a dental image landmark;
   a bounding box component configured to generate an image confidence score for the dental image and/or a dental image landmark;
   an image classification component configured to generate a dental image confidence score;
   an object classification component configured to generate a dental object confidence score;
   a value mechanism component configured to generate a treatment confidence score;
   a value mechanism component configured to generate a dental product confidence score;
   a semantic segmentation component configured to generate a semantic segmentation of a dental image and/or a dental image landmark;
   an instance segmentation component configured to generate an instance segmentation of a dental image and/or a dental image landmark;
   a supervised learning component configured to annotate a dental image and/or a dental image landmark;
   an unsupervised learning component configured to annotate a dental image and/or a dental image landmark;
   a recurrent neural network component (RNN) configured to analyze a dataset;
   an independent neural network component (INDRNN) configured to analyze a dataset;
   a deep forest decision tree configured to analyze a dataset;
   a processor configured for a system of memory of dataset;
   a processor configured for a system of artificial intelligence with memory;
   a processor configured for a system of reactive memory;
   a processor configured for a system of non-reactive memory;
   a processor configured for a system of rewards training;
   a processor configured for a system of transfer learning;
   a processor configured with an object tracking mechanism configured to track objects in a dental image and/or a dental image landmark;
   a processor configured for natural language processing (NLP);
   a processor configured to upload and/or download at least one of: an exchange, a transmission, a storage of a dataset with at least one of: a server, a desktop computer, a workstation, a laptop computer, a cell phone, a tablet, a mobile device, a cloud-based storage service;
   a processor configured for at least one of: a dental professional, a health care professional, an individual, an e-commerce organization to process a transaction of at least one of: an exchange, a transfer, a buy, a sell at least one of: a dental image, a dental image landmark, a dataset wherein a transaction is at least one of: business to business (B2B), business to consumer (B2C), consumer to business (C2B), consumer to consumer (C2C), business to administration (B2A), consumer to administration (C2A) in exchange for at least one of: a currency, data, a discount, a product, goods, a software, an application, an advertisement.

6. The aggregator server of claim 1, wherein the supervised and/or unsupervised learning of a dental image and/or a dental image landmark with a deep neural network occurs concurrently with learning a plurality of a supervised and/or unsupervised annotated dental image anatomy dataset and/or supervised and/or unsupervised annotated dental image pathology datasets;
   supervised and/or unsupervised learning of a dental image and/or a dental image landmark with a deep neural network occurs concurrently with learning a plurality of a supervised and/or unsupervised dental image landmark dataset;
   supervised and/or unsupervised learning of a dental image and/or a dental image landmark with a deep neural network occurs concurrently with learning a plurality of a supervised and/or unsupervised annotated dental image landmark dataset and/or a supervised and/or unsupervised annotated dental treatment dataset;
   supervised and/or unsupervised learning of a dental image and/or a dental image landmark with a deep neural network occurs concurrently with learning a plurality of an annotated dental image treatment dataset and/or an artificial intelligence dental dataset;
   supervised and/or unsupervised learning of a dental image and/or a dental image landmark with a deep neural network occurs concurrently with learning a plurality of an individual information dataset;
   supervised and/or unsupervised learning of a dental image and/or dental image landmark with a deep neural network occurs concurrently with learning a plurality of an annotated dental product dataset and/or an artificial intelligence dental dataset.

7. The aggregator server of claim 1, wherein at least one of: a dental image, a dental image landmark, a dataset is configured to compensate for distorted and/or missing image information.

8. The aggregator server of claim 1, wherein the dental image and/or the dental image landmark is processed with at least one of:
   at least one deep neural network layer configured to match and identify an annotated dental image anatomy;
   at least one deep neural network layer configured to match and identify an annotated dental image pathology;
   at least one deep neural network layer configured to match and identify an annotated dental image supervised and/or unsupervised dental image landmark dataset;

at least one deep neural network layer configured to match and identify an annotated dental landmark dataset;

at least one deep neural network layer configured to match and identify an annotated dental treatment dataset;

at least one deep neural network layer configured to match and identify a patient dataset and/or an individual information dataset;

at least one deep neural network layer configured to match and identify an artificial intelligence dental image dataset;

at least one deep neural network layer configured to match and identify an annotated dental product dataset.

9. The aggregator server of claim 1, wherein a dental professional and/or a health care professional includes a dentist, a hygienist, a dental assistant, a dental staff member, a dental laboratory technician, a physician, a nurse, a medical technician, a veterinarian, a veterinarian professional;

wherein an individual includes an individual, a guardian, a group, an employee;

wherein an e-commerce organization includes a business, a business entity, a business owner, an employer, a wholesaler, a retailer, group, a research entity, a law enforcement entity, a public administration entity, a government agency, an administrator, an administrator entity, a governing agency, a bioinformatics service, an insurance company, a cloud-based storage service.

10. The of claim 1, wherein the dataset is configured to produce:

a multiple treatment option aid for at least one of: a dental provider, a health care professional, an individual, an e-commerce organization;

a multiple treatment demonstration aid for at least one of: a dental provider, a health care professional, an individual, an e-commerce organization;

process and display a multiple treatment option aid and/or a multiple treatment demonstration aid as at least one of: a number, a percentage, a percent, a proportion, a ratio, a graph, a color, an image, a score, a grade, a count, a rate, an average, a figure, an outline, an area, a shading;

provide and/or store a multiple treatment option aid and/or a multiple treatment demonstration aid to a client device, wherein a client device includes a server, a desktop computer, a workstation, a laptop computer, a cell phone, a tablet, a mobile device, a cloud-based storage service;

provide at least one of: a multiple treatment option aid, a multiple treatment demonstration, an artificial intelligence dental dataset, a change in an individual address, to at least one of: a financing organization, a dental specialist, a medical specialist which may process a transaction of at least one of: an exchange, a transfer, a buy, a sell over a communication network.

11. The of claim 1, wherein the aggregator server is configured to provide at least one of: an annotated diagnostic treatment aid, an annotated treatment demonstration aid, a dental product recommendation; wherein a dental product recommendation may include at least one of: a specific orthodontic aligner, a specific dental implant, a specific crown, a specific membrane, a specific graft, a specific screw, a specific composite, a specific amalgam, a specific dental instrument to a dental professional, a health care professional, an individual, an e-commerce organization.

12. An aggregator server for providing dental images processed with artificial intelligence for e-commerce, the aggregator server comprising:

a computer vision component configured to analyze the dental image and/or dental image landmark;

a memory configured to store instructions associated with an aggregator service server; a processor configured to bidirectional exchange at least one of: a dental image, a dental image landmark, a dataset, with a mobile device;

a processor configured to bidirectional exchange at least one of: a dental image, a dental image landmark, a dataset with a cell phone;

a processor coupled to the computer vision component and the memory, the processor executing the instructions associated with the aggregator service server, wherein the aggregator server includes:

an image processing engine configured to: receive a dental image and/or dental image landmark;

process a dental image and/or a dental image landmark with artificial intelligence to generate an image confidence score;

process a dental image and/or a dental image landmark with artificial intelligence to generate an object confidence score;

process a dental image and/or a dental image landmark with a deep neural network and match and/or identify to a supervised and/or unsupervised annotated anatomy dataset;

process a dental image and/or a dental image landmark with a deep neural network and match and/or identify to a supervised and/or unsupervised annotated pathology dataset;

process a dental image and/or a dental image landmark with a deep neural network and match and/or identify to a supervised and/or unsupervised dental landmark dataset;

process a dental image and/or a dental image landmark with a deep neural network and match and/or identify to a supervised and/or unsupervised annotated dental landmark dataset;

process a dental image and/or a dental image landmark with a deep neural network and match and/or identify to a supervised and/or unsupervised annotated dental treatment dataset;

process a dental image and/or a dental image landmark with a deep neural network and match and/or identify to an annotated dental image treatment dataset;

merge at least one of: a matched and/or identified dental image, dental image landmark, a supervised and/or unsupervised annotated dental image anatomy dataset, a supervised and/or unsupervised annotated dental image pathology dataset, a supervised and/or unsupervised dental image landmark dataset, a supervised and/or annotated dental image landmark dataset, a supervised and/or unsupervised dental treatment dataset to an annotated dental treatment dataset;

merge an individual information dataset with an annotated dental image treatment dataset to produce an artificial intelligence dental dataset;

process a dental image and/or a dental image landmark with an artificial intelligence dental dataset and a supervised and/or unsupervised dental product dataset to produce a multiple treatment option aid and/or a multiple treatment demonstration aids;

process at least one of: a dental image, a dental image landmark, an artificial intelligence dental dataset with a dental product dataset to produce product recommendations;

process at least one of: a dental image, a dental image landmark, an artificial intelligence dental dataset with a provider dataset to produce a dental professional referral and/or a medical professional referral;

wherein a provider dataset may include a dental professional and/or dental specialist, a health care professional and/or a health care specialist, a dentist, dental specialist, hygienist, a dental assistant, dental staff member, a dental laboratory technician, a physician, physician specialist, a nurse, a medical technician, a veterinarian, a veterinarian professional;

provide a multiple treatment option aid and/or a multiple treatment demonstration aids to at least one of: a dental professional, a health care professional, an individual, an e-commerce organization;

identify and correct a discrepancy between at least one of: a dental image, a dental image landmark, dataset;

format the dataset based on another dataset associated with an individual dataset;

merge an individual dataset into an annotated dental image treatment dataset to produce an artificial intelligence dental dataset;

provide an artificial intelligence dataset to at least one of: a dental professional, a health professional, an individual, an e-commerce organization;

process a transaction of at least one of: an exchange, a transfer, a buy, a sell with at least one of: a dental image, a dental image landmark, a dataset; where in a dataset includes at least one of: a dental image, dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, a supervised and/or unsupervised annotated dental treatment dataset, an annotated dental image treatment dataset, an artificial intelligence dental dataset, an individual information dataset over a communication network, wherein a communication network includes at least one of: the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

13. The of claim 12, wherein a dental professional and/or a health care professional includes a dentist, a hygienist, a dental assistant, a dental staff member, a dental laboratory technician, a physician, a nurse, a medical technician; wherein an individual includes an individual, a guardian, a group, an employee; wherein an e-commerce organization includes a business, a business entity, a business owner, an employer, a wholesaler, a retailer, group, a research entity, a law enforcement entity, a public administration entity, a government agency, an administrator, an administrator entity, a governing agency, a bioinformatics service, an insurance company, a cloud-based storage service.

14. The aggregator server of claim 12, wherein the dataset that is provided to at least one of: a dental professional, a health care professional, an individual, an e-commerce organization upon a process to:
verify a compliance of an individual and/or an individual dataset with a regulatory policy;
verify an authorization by the individual to analyze the dental image and dataset;
authenticate an individual to process a transaction of at least one of: an exchange, a transfer, a buy, a sale of a dataset for at least one of: a currency, data, a discount, a product, goods, a software, an application, an advertisement;
match and identify human remains to at least one of: a dental image, a dental image landmark, dataset and provide to a governing agency;
locate an individual dental treatment location and provide to a governing agency.

15. The aggregator server of claim 12, where the individual dataset includes at least one of: an age, a first name, a gender, a middle initial, a last name, a date of birth, a zip code, an address, a cell phone number, a landline number, a current medication, a previous medication, a social security number, a marital status, an insurance, an insurance identification number, an email address, a change of insurance, a change of employment, a change of address, a change of zip code, a change of the previous medication, a change of the marital status, a change of gender.

16. The aggregator server of claim 12, wherein the e-commerce organization includes a dental insurance service, and wherein the dental insurance service provides an insurance dataset including at least one of: an American dental association (ADA) code, a date, a claim identifier, a claim number, a duplicate claim associated with the claim identifier, a provider national identification number, a provider's state license number, a provider identification number may be correlated to an insurance dataset and merged to an artificial intelligence dental dataset.

17. The aggregator server of claim 12, wherein the e-commerce organization includes a bioinformatics service, and wherein the bioinformatics service provides a bioinformatics dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, a diabetes diagnosis to further analyze and integrate the bioinformatics dataset and merge to an artificial intelligence dental dataset.

18. A method of providing dental images processed with artificial intelligence for e-commerce, the method comprising:
receiving a dental image and/or a dental image landmark of an individual from a dental professional, a health professional, an individual, an e-commerce organization;
processing the dental image and/or dental image landmark with a supervised and/or unsupervised annotated dental image anatomy dataset and/or a supervised and/or unsupervised annotated dental image pathology dataset;

match and identify a dental image and/or dental image landmark anatomy and/or pathology to a supervised and/or unsupervised dental image landmark dataset;

match and identify a supervised and/or unsupervised dental image landmark dataset to a supervised and/or unsupervised annotated dental image landmark dataset and/or a supervised and/or unsupervised annotated dental treatment dataset;

process and merge an unsupervised annotated dental image landmark dataset and/or a supervised and/or unsupervised annotated dental treatment dataset to an annotated dental image treatment dataset;

merge an annotated dental image treatment dataset with an individual information dataset to produce an artificial intelligence dental dataset;

match and identify an annotated dental product dataset with an artificial intelligence dental dataset to produce multiple treatment options and/or product recommendation and/or no recommendations;

querying and receive at least one of: a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, a supervised and/or unsupervised annotated dental treatment dataset, an annotated dental image treatment dataset, an artificial intelligence dental dataset, an individual information dataset, an annotated dental product dataset provide to a dental professional, a health professional, an individual, an e-commerce organization.

19. The aggregator server of claim 18, wherein a dental professional and/or a health care professional includes a dentist, a hygienist, a dental assistant, a dental staff member, a dental laboratory technician, a physician, a nurse, a medical technician;
wherein an individual includes an individual, a guardian, a group, an employee;
where in an e-commerce organization includes a business, a business entity, a business owner, an employer, a wholesaler, a retailer, group, a research entity, a law enforcement entity, a public administration entity, a government agency, an administrator, an administrator entity, a governing agency, a bioinformatics service, an insurance company, a cloud-based storage service.

20. The aggregator server of claim 18, wherein the aggregator server is configured to: process a transaction of at least one of: an exchange, a transfer, a buy, a sell with at
least one of: a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, a supervised and/or unsupervised annotated dental treatment dataset, an annotated dental image treatment dataset, an artificial intelligence dental dataset, an individual information dataset over a communication network, wherein a communication network includes at least one of: the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

Details related to Aspect 1: A dental professional, a health professional, an individual, an e-commerce organization may use supervised learning, unsupervised learning and/or artificial intelligence to process a transaction of least one: an exchange, a transfer, a buy, a sell of at least one of: a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, an annotated dental image treatment dataset, an artificial intelligence dental dataset, an individual information dataset over a communication network, wherein a communication network includes at least one of: the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

Details related to Aspects 9, 13 and 19. An example of a dental professional and/or a health care professional includes a dentist, a hygienist, a dental assistant, a dental staff member, a dental laboratory technician, a physician, a nurse, a medical technician, a veterinarian, a veterinarian professional;

An example of an individual includes an individual, a guardian, a group, an employee; An example of e-commerce organization includes a business, a business entity, a business owner, an employer, a wholesaler, a retailer, group, a research entity, a law enforcement entity, a public administration entity, a government agency, an administrator, an administrator entity, a governing agency, a bioinformatics service, an insurance company, a cloud-based storage service.

Details related to Aspects 1 and 15. An individual dataset includes least one of: an age, a first name, a gender, a middle initial, a last name, a date of birth, a zip code, an address, a cell phone number, a landline number, a current medication, a previous medication, a social security number, a marital status, an insurance, an insurance identification number, an email address, a change of insurance, a change of employment, a change of address, a change of zip code, a change of the previous medication, a change of the marital status, a change of gender.

Details related to Aspect 2. An e-commerce transaction includes at least one of: business to business (B2B), business to consumer (B2C), consumer to business (C2B), consumer to consumer (C2C), business to administration (B2A) and consumer to administration (C2A).

Details related to Aspect 3. A dental image is obtained from at least one of: a digital x-ray, a digital image, a cell phone captured image, a photographic image, toothbrush with imaging device, toothbrush with imaging device a being camera, a film based x-ray, a digitally scanned x-ray, a digitally captured x-ray, an intraoral scanner, a scintillator technology-based image, a trans-illumination image, a fluorescence technology-based image, a blue fluorescence technology-based image, a laser-based technology-based image, a magnetic resonance image (MRI), a computed tomography (CT) scan based image, a cone-beam computed tomography (CBCT) image.

Details related to Aspect 4. A dental professional, a health care professional, an individual, an e-commerce organization may utilize an image capture device or a data storage device, and wherein the captured image device includes one or more of: an x-ray equipment, a digital camera, an intraoral camera, a cell phone camera, an intraoral scanner, a scintillator counter, an indirect or direct flat panel detector (FPD), a charged coupled device (CCD), a phosphor plate radiography device, a picture archiving and communication system (PACS), a photo-stimulatable phosphor (PSP) device, a wireless complementary metal-oxide-semiconductor (CMOS) device.

An individual may utilize an image capture device or a data storage device, and wherein the captured image device includes one or more of: a camera, a digital camera, a cell phone camera, a photographic image, a toothbrush with an imaging device, toothbrush with imaging device being the camera, an intraoral camera.

Details related to Aspect 5. An aggregator server is configured to execute an aggregator server to process a dental image and/or a dental image landmark with at least one of:
  a sliding window component configured to analyze a dental image and/or a dental image landmark,
  a multiple grid component configured to divide and analyze a dental image and/or a dental image landmark,
  a bounding box component configured to analyze a dental image and/or a dental image landmark,
  a bounding box component configured to generate an image confidence score for the dental image and/or a dental image landmark,
  an image classification component configured to generate a dental image confidence score,
  an object classification component configured to generate a dental object confidence score,
  a value mechanism component configured to generate a treatment confidence score,
  a value mechanism component configured to generate a dental product confidence score,
  a semantic segmentation component configured to generate a semantic segmentation of a dental image and/or a dental image landmark,
  an instance segmentation component configured to generate an instance segmentation of a dental image and/or a dental image landmark,
  a supervised learning component configured to annotate a dental image and/or a dental image landmark,
  an unsupervised learning component configured to annotate a dental image and/or a dental image landmark, a recurrent neural network component (RNN) configured to analyze a dataset,
  an independent neural network component (INDRNN) configured to analyze a dataset,
  a deep forest decision tree configured to analyze a dataset, a processor configured for a system of memory of dataset, a processor configured for a system of artificial intelligence with memory,
  a processor configured for a system of reactive memory, a processor configured for a system of non-reactive memory, a processor configured for a system of rewards training, a processor configured for a system of transfer learning, a processor configured with an object tracking mechanism configured to track objects in a dental image and/or a dental image landmark, a processor configured for natural language processing (NLP). A processor configured to upload and/or download at least one of: an exchange, a transmission, a storage of a dataset with at least one of: a server, a desktop computer, a workstation, a laptop computer, a cell phone, a tablet, a mobile device, a cloud-based storage service.

A processor configured for at least one of: a dental professional, a health care professional, an individual, an e-commerce organization to process a transaction of at least one of: an exchange, a transfer, a buy, a sell at least one of: a dental image, a dental image landmark, a dataset wherein a transaction is at least one of: business to business (B2B), business to consumer (B2C), consumer to business (C2B), consumer to consumer (C2C), business to administration (B2A), consumer to administration (C2A) in exchange for at least one of: a currency, data, a discount, a product, goods, a software, an application, an advertisement.

Details related to Aspect 6. An aggregator server is configured to execute an aggregator server to process a supervised and/or unsupervised learning of a dental image and/or a dental image landmark with a deep neural network occurs concurrently with learning a plurality of dental image(s), a dental image landmark(s), a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, annotated dental image treatment dataset, an artificial intelligence dental dataset and/or individual information dataset.

Details related to Aspect 7. An aggregator server is configured to execute an aggregator server to compensate for distorted and/or missing image information.

Details related to Aspect 8. An aggregator server is configured to execute an aggregator server to match and identify a dental image and/or the dental image landmark with at least
  one deep neural network layer to at least one of:
    annotated dental image anatomy, identify an annotated dental image pathology, an annotated dental image supervised and/or unsupervised dental image landmark dataset, an annotated dental landmark dataset, an annotated dental treatment dataset, identify a patient dataset and/or an individual information dataset, an artificial intelligence dental image dataset, a dental product dataset.

Details related to Aspect 10. An aggregator saver is configured to execute an aggregator server is configured to produce:
  a multiple treatment option aid for at least one of: a dental provider, a health care professional, an individual, an e-commerce organization. A multiple treatment demonstration aids for at least one of: a dental provider, a health care professional, an individual, an e-commerce organization. Provide and/or store a multiple treatment option aid and/or a multiple treatment demonstration aids to a client device, wherein a client device includes a server, a desktop computer, a workstation, a laptop computer, a cell phone, a tablet, a mobile device, a cloud-based storage service.

Details related to Aspect 11. An aggregator server is configured to execute an aggregator service server that is configured to provide an annotated diagnostic treatment aid and/or annotated treatment demonstration aid to at least one of: a dental professional, a health care professional, an individual, an e-commerce organization.

Details related to Aspect 12. An aggregator server for providing dental images processed with artificial intelligence for e-commerce, the aggregator server comprising: a computer vision component, a memory configured to store instructions, a processor configured to bidirectional exchange at least one of: a dental image, a dental image landmark, a dataset, with a mobile device, a processor configured to bidirectional exchange at least one of: a dental image, a dental image landmark, a dataset with a cell phone, a processor coupled to the computer vision component and the memory, the processor executing the instructions associated with the aggregator server, wherein the aggregator server includes: an image processing engine configured to:

receive a dental image and/or dental image landmark, process a dental image and/or a dental image landmark with at least one of the following: an artificial intelligence to generate an image confidence score, an artificial intelligence to generate an object confidence score, a deep neural network and match and/or identify to a supervised and/or unsupervised anatomy dataset, a deep neural network and match and/or identify to a supervised and/or unsupervised pathology dataset, a deep neural network and match and/or identify to a supervised and/or unsupervised dental landmark dataset, a deep neural network and match and/or identify to a supervised and/or unsupervised annotated dental landmark dataset, a deep neural network and match and/or identify to a supervised and/or unsupervised annotated dental treatment dataset, a deep neural network, and match and/or identify to an annotated dental image treatment dataset.

Merge at least one of: a matched and/or identified dental image, dental image landmark, a supervised and/or unsupervised annotated dental image anatomy dataset, a supervised and/or unsupervised annotated dental image pathology dataset, a supervised and/or unsupervised dental image landmark dataset, a supervised and/or annotated dental image landmark dataset, a supervised and/or unsupervised dental treatment dataset to an annotated dental treatment dataset. Merge an individual information dataset with an annotated dental image treatment dataset to produce an artificial intelligence dental dataset. Process a dental image and/or a dental image landmark with an artificial intelligence dental dataset and a supervised and/or unsupervised dental product dataset to produce a multiple treatment option aid and/or a multiple treatment demonstration aids. Process at least one of: a dental image, a dental image landmark, an artificial intelligence dental dataset with an annotated dental product dataset to produce product recommendations.

Process at least one of: a dental image, a dental image landmark, an artificial intelligence dental dataset with a provider dataset to produce a dental professional referral and/or a medical professional referral.

Where in a provider dataset may include a dental professional and/or dental specialist, a health care professional and/or a health care specialist, a dentist, dental specialist, hygienist, a dental assistant, dental staff member, a dental laboratory technician, a physician, physician specialist, a nurse, a medical technician, a veterinarian, a veterinarian professional. Provide a multiple treatment option aid and/a multiple treatment demonstration aids to at least one of: a dental professional, a health professional, an individual, an e-commerce organization. Identify and correct a discrepancy between at least one of: a dental image, a dental image landmark, dataset. Format the dataset based on another dataset associated with an individual dataset. Merge an individual dataset into an annotated dental image treatment dataset to produce an artificial intelligence dental dataset.

Provide an artificial intelligence dataset to at least one of: a dental professional, a health professional, an individual, an e-commerce organization.

Process a transaction of at least one of: an exchange, a transfer, a buy, a sell with at least one of: a dental image, a dental image landmark, a dataset; where in a dataset includes at least one of: a dental image, dental image landmark, a supervised and/or unsupervised annotated dental image anatomy dataset, a supervised and/or unsupervised annotated dental image pathology dataset, a supervised and/v 6 unsupervised dental image landmark dataset, a supervised and/or unsupervised annotated dental image landmark dataset, a supervised and/or unsupervised annotated dental treatment dataset, an annotated dental image treatment dataset, an artificial intelligence dental dataset, an individual information dataset over a communication network, wherein a communication network includes at least one of: the Internet, an intranet, an extranet, an internet, an internet transaction service, an online transaction service, a mobile network, a wireless network, a cloud platform, an online transaction processing (OLTP) service, an online analytical processing (OLAP) service, a transaction platform.

Details related to Aspect 14. The aggregator server may execute the aggregator service server to provide to at least one of: a dental professional, a health care professional, an individual, an e-commerce organization upon a process to:

verify a compliance of an individual and/or an individual dataset with a regulatory policy;

verify an authorization by the individual to analyze the dental image and dataset Authenticate an individual to process a transaction of at least one of: an exchange, a transfer, a buy, a sell of a dataset for at least one of: a currency, data, a discount, a product, goods, a software, an application, an advertisement. Match and identify human remains to at least one of: a dental image, a dental image landmark, dataset and provide to a governing agency. Locate an individual dental treatment location and provide to a governing agency.

Details related to Aspects 15 and 1. The aggregator server and/or the aggregate server may process an individual dataset;

where the individual dataset includes at least one of an age, a first name, a gender, a middle initial, a last name, a date of birth, a zip code, an address, a cell phone number, a landline number, a current medication, a previous medication, a social security number, a marital status, an insurance, an insurance identification number, an email address, a change of insurance, a change of employment, a change of zip code, a change of the previous medication, a change of the marital status, a change of gender.

Details related to Aspect 16. An aggregator server may process information to and from a dental insurance service. A dental insurance service may include an insurance company and/or a claims data warehouse. A dental insurance service may be an insurance company.

The insurance machine learning service may be provided by a dental insurance and/or a medical insurance organization. A dental image, a dental image landmark or a dataset may be provided by a dental professional, a medical professional, an individual, an e-commerce organization. Wherein the e-commerce organization includes a dental insurance service, and wherein the dental insurance service provides an insurance dataset including at least one of: an American dental association (ADA) code, a date, a claim identifier, a claim number, a duplicate claim associated with the claim identifier, a provider national identification number, a provider's state license number, a provider identification number may be correlated to an insurance dataset and merged to an artificial intelligence dental dataset.

Details related to Aspect 17. An aggregator server may process information for a bioinformatics service. A bioinformatics service may be a genetic testing service and/or a genotyping service. The bioinformatics service may be provided by a bioinformatics organization (such as a personal genomic or research organization). A dental professional, a health professional, an individual, an e-commerce organization may correlate a dental image, a dental image landmark, a dataset to a bioinformatics dataset. An e-commerce organization includes a bioinformatics service, and wherein the bioinformatics service provides a bioinformatics dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, a diabetes diagnosis to further analyze and integrate the bioinformatics dataset and merge to an artificial intelligence dental dataset.

Details related to Aspect 10. The artificial intelligence dental dataset may match and process patient compliance factors by querying dental software data field(s) by at least one or more of: insurance maximum, remaining benefits, missed appointments, rescheduled appointments. In another scenario, predetermined question(s) may be queried to profile patient compliance by at least one or more of: dental phobia, financial challenges, lifestyle changes, business plans, travel plans, illness, injury. In cases of financial obstacles to treatment, the artificial intelligence dental treatment dataset may suggest specific third party financing companies. Based on predetermined questions, the artificial intelligence dental dataset may also suggest sedation dentistry.

Details related to Aspect 10. The artificial intelligence dental dataset may recommend treatment products, goods, services and specialist referrals for multiple treatment options based on dental treatment and/or dental product confidence scores to dental professionals, health care professionals, individuals, e-commerce providers.

Details related to Aspect 10. The artificial intelligence dental dataset may recognize when a patient has moved and/or changed address locations and recommend new dentists and dental specialists based on geographic location such as Global Position System (GPS).

Details related to Aspect 10. The artificial intelligence dental dataset may provide the correlated annotated dental images and the patient's datasets to a dental specialist that may buy and/or sell this information over a communication network such as the internet. Further, the artificial intelligence dental dataset's referral may be based on geographic location such as Global Position System (GPS).

Details related to Aspect 14. The artificial intelligence dental dataset may verify the identity of an individual from his or hers correlated annotated dental image dataset. This verification process may be provided to government agencies such as Home Land Security.

Details related to Aspect 14. The artificial intelligence dental dataset may identify human remains by comparing dental image of the human remains with of at least one of: a dental image, a dental image landmark, a supervised and/or unsupervised annotated dental image anatomy dataset, a supervised and/or unsupervised annotated dental image pathology dataset, a supervised and/or unsupervised dental image landmark dataset, a supervised and/or unsupervised annotated dental image landmark dataset, supervised and/or unsupervised annotated dental treatment dataset, annotated dental image treatment dataset, an artificial intelligence dental dataset, an individual information dataset.

Details related to Aspect 14. The artificial intelligence dental dataset may identify a patient's geographic dental visit movements with the correlated annotated image dataset. This geographic dental visit movement may be provided to a government agency such as Child Services to track abducted children.

The following is claimed:

1. A method of generating a dental recommendation based on image processing, wherein the method comprising:
   receiving, using a communication device, at least one patient data comprising at least one image from at least one patient device;
   wherein the at least one patient device may include at least one user device;
   retrieving, using a storage device, at least one dental dataset;
   analyzing, using a processing device, the at least one patient data and the at least one dental dataset, wherein the at least one dental dataset is associated with the at least one patient data, wherein the at least one dental dataset comprises a classified dental image dataset;
   wherein the analyzing of the at least one patient data and the at least one dental dataset is based on at least one first artificial intelligence model;
   generating, using the processing device, at least one landmark based on the analyzing, wherein the at least one landmark comprises at least one dental characteristic associated with the at least one patient data;
   retrieving, using the storage device, at least one dental reference dataset;
   image processing, using the processing device, the at least one landmark and the at least one dental reference dataset;
   wherein the image processing of the at least one landmark and the at least one dental reference dataset is based on at least one second artificial intelligence model, wherein the at least one second artificial intelligence model is configured for determining of the dental recommendation;
   determining, using the processing device, at least one dental recommendation based on the processing;
   transmitting, using the communication device, the at least one dental recommendation to at least one external device; and
   storing, using the storage device, the at least one dental recommendation.

2. The method of claim 1, wherein the at least one dental recommendation comprises a dental product recommendation and a dental treatment recommendation, wherein the method further comprising:
   transmitting, using the communication device, the at least one dental recommendation and the at least one patient data to at least one expert device associated with at least one expert;
   receiving, using the communication device, a first confidence score from the at least one expert device, wherein the first confidence score is associated with the at least one dental recommendation; and
   transmitting, using the communication device, the first confidence score to the at least one external device.

3. The method of claim 2 further comprising:
   updating, using the processing device, the at least one dental reference dataset with the at least one patient data and the at least one dental recommendation based on the first confidence score;

generating, using the processing device, at least one updated reference dataset based on the updating of the at least one dental reference dataset; and storing, using the storage device, the at least one updated reference dataset.

4. The method of claim 1 further comprising:

receiving, using the communication device, an order from the at least one patient device, wherein the order is associated with the at least one dental recommendation;

transmitting, using the communication device, the order to the at least one external device;

receiving, using the communication device, a response corresponding to the order from the at least one external device; and transmitting, using the communication device, the response to the at least one patient device.

5. The method of claim 1 further comprising:

transmitting, using the communication device, the at least one patient data and the at least one landmark to the at least one expert device;

receiving, using the communication device, a second confidence score from the at least one expert device, wherein the second confidence score is associated with the at least one landmark; and transmitting, using the communication device, the second confidence score to the at least one external device.

6. The method of claim 1 further comprising:

analyzing, using the processing device, the at least one patient data and the at least one dental dataset;

generating, using the processing device, a validity notification corresponding to the at least one patient data based on the analyzing, wherein the validity notification is associated with a measure of approval of the at least one patient data; and transmitting, using the communication device, the validity notification to the at least one external device.

7. The method of claim 1, wherein the at least one external device comprises at least one first user device associated with at least one first user, wherein the method further comprising:

transmitting, using the communication device, a request to the at least one first user device;

receiving, using the communication device, at least one first user data from the at least one first user device;

retrieving, using the storage device, at least one regulatory data based on the at least one first user;

analyzing, using the processing device, the at least one first user data based on the at least one regulatory data;

generating, using the processing device, a notification corresponding to the at least one first user based on the analyzing of the at least one first user data; and transmitting, using the communication device, the notification to at least one of the at least one patient device and the at least one external device.

8. The method of claim 1, wherein the classified dental image dataset comprises at least one of a classified dental image anatomy dataset and a classified dental image pathology dataset.

9. The method of claim 1, wherein the at least one first artificial intelligence model is configured for identifying of the at least one dental characteristic associated with the at least one patient data.

10. The method of claim 1, wherein the one user device may include a smartphone, a tablet, a mobile device, a computer, a laptop.

11. A system of generating a dental recommendation based on image processing, the system comprising:

a communication device configured for:
  receiving at least one patient data comprising at least one image from at least one patient device;
  wherein the at least one patient device may include at least one user device;
  transmitting at least one dental recommendation to at least one external device;

a processing device configured for:
  analyzing the at least one patient data and at least one dental dataset, wherein the at least one dental dataset is associated with the at least one patient data, wherein the at least one dental dataset comprises a classified dental image dataset;
  wherein the analyzing of the at least one patient data and the at least one dental dataset is based on at least one first artificial intelligence model;
  generating at least one landmark based on the analyzing, wherein the at least one landmark comprises at least one dental characteristic associated with the at least one patient data;

image processing the at least one landmark and at least one dental reference dataset;
  wherein the image processing of the at least one landmark and the at least one dental reference dataset is based on at least one second artificial intelligence model, wherein the at least one second artificial intelligence model is configured for determining of the at least one dental recommendation;
  determining the at least one dental recommendation based on the image processing;

a storage device configured for:
  retrieving the at least one dental dataset;
  retrieving the at least one dental reference dataset; and
  storing the at least one dental recommendation.

12. The system of 11, wherein the at least one dental recommendation comprises a dental product recommendation and a dental treatment recommendation, wherein the system further comprising:

the communication device configured for:
  transmitting the at least one dental recommendation and the at least one patient data to at least one expert device associated with at least one expert;
  receiving a first confidence score from the at least one expert device, wherein the first confidence score is associated with the at least one dental recommendation; and
  transmitting the first confidence score to the at least one external device.

13. The system of claim 12 further comprising:

the processing device configured for:
  updating the at least one dental reference dataset with the at least one patient data and the at least one dental recommendation based on the first confidence score; and
  generating at least one updated reference dataset based on the updating of the at least one dental reference dataset; and the storage device configured for storing the at least one updated reference dataset.

14. The system of claim 11 further comprising:
the communication device configured for:
- receiving an order from the at least one patient device, wherein the order is associated with the at least one dental recommendation;
- transmitting the order to the at least one external device;
- receiving a response corresponding to the order from the at least one external device; and
- transmitting the response to the at least one patient device.

15. The system of claim 11 further comprising:
the communication device configured for:
- transmitting the at least one patient data and the at least one landmark to the at least one expert device;
- receiving a second confidence score from the at least one expert device, wherein the second confidence score is associated with the at least one landmark; and
- transmitting the second confidence score to the at least one external device.

16. The system of claim 11 further comprising:
the communication device configured for transmitting a validity notification to the at least one external device; and
the processing device configured for:
- analyzing the at least one patient data and the at least one dental dataset; and
- generating the validity notification corresponding to the at least one patient data based on the analyzing, wherein the validity notification is associated with a measure of approval of the at least one patient data.

17. The system of claim 11, wherein the at least one external device comprises at least one first user device associated with at least one first user, wherein the system further comprising:
the communication device configured for:
- transmitting a request to the at least one first user device of the at least one external device;
- receiving at least one first user data from the at least one first user device; and
- transmitting a notification to at least one of the at least one patient device and the at least one external device;
the processing device configured for:
- analyzing, using the processing device, the at least one first user data based on at least one regulatory data; and
- generating, using the processing device, the notification corresponding to the at least one first user based on the analyzing of the at least one first user data; and
the storage device configured for retrieving the at least one regulatory data based on the at least one first user.

18. The system of claim 11, wherein the classified dental image dataset comprises at least one of a classified dental image anatomy dataset and a classified dental image pathology dataset.

19. The system of claim 11,
wherein the at least one first artificial intelligence model is configured for identifying of the at least one dental characteristic associated with the at least one patient data.

20. A method of generating a dental recommendation based on image processing, wherein the method comprising:
- receiving, using an aggregator server, at least one patient data comprising at least one image from at least one patient device;
- wherein the at least one patient device may include at least one user device;
- retrieving, using a storage device, at least one dental dataset;
- analyzing, using a processing device, the at least one patient data and the at least one dental dataset, wherein the at least one dental dataset is associated with the at least one patient data, wherein the at least one dental dataset comprises a classified dental image dataset;
- wherein the analyzing of the at least one patient data and the at least one dental dataset is based on at least one first artificial intelligence model;
- generating, using the processing device, at least one landmark based on the analyzing, wherein the at least one landmark comprises at least one dental characteristic associated with the at least one patient data;
- retrieving, using the storage device, at least one dental reference dataset;
- image processing, using the processing device, the at least one landmark and the at least one dental reference dataset;
- wherein the image processing of the at least one landmark and the at least one dental reference dataset is based on at least one second artificial intelligence model, wherein the at least one second artificial intelligence model is configured for determining of the at least one dental recommendation;
- determining, using the processing device, at least one dental recommendation based on the processing;
- wherein the at least one landmark may be displayed as at least one of a number, a percentage, a percent, a proportion, a ratio, a graph, a color, an image, a score, a grade, a count, a rate, an average, a figure, an outline, an area, or a shading;
- transmitting, using the aggregator server, the at least one dental recommendation to at least one external device; and
- storing, using the storage device, the at least one dental recommendation.

* * * * *